(12) United States Patent
Losso et al.

(10) Patent No.: US 11,224,612 B1
(45) Date of Patent: Jan. 18, 2022

(54) **GLYCOSAMINOGLYCANS FROM *ALLIGATOR MISSISSIPPIENSIS***

(71) Applicant: Board of Supervisors of Louisiana State University and Agricultural and Mechanical College, Baton Rouge, LA (US)

(72) Inventors: Jack N. Losso, Baton Rouge, LA (US); Jose Daniel Estrada Andino, Minneapolis, MN (US)

(73) Assignee: Board of Supervisors of Louisiana State University and Agricultural and Mechnical College, Baton Rouge, LA (US)

( * ) Notice: Subject to any disclaimer, the term of this patent is extended or adjusted under 35 U.S.C. 154(b) by 24 days.

(21) Appl. No.: 16/507,808

(22) Filed: Jul. 10, 2019

Related U.S. Application Data

(63) Continuation-in-part of application No. 16/223,908, filed on Dec. 18, 2018, now abandoned.

(60) Provisional application No. 62/612,772, filed on Jan. 2, 2018.

(51) Int. Cl.
*A61K 31/728* (2006.01)
*A61K 9/00* (2006.01)
*A61K 9/16* (2006.01)

(52) U.S. Cl.
CPC .......... *A61K 31/728* (2013.01); *A61K 9/0073* (2013.01); *A61K 9/16* (2013.01)

(58) Field of Classification Search
None
See application file for complete search history.

(56) References Cited

U.S. PATENT DOCUMENTS 7,109,300 B2    9/2006  Losso

OTHER PUBLICATIONS

Estrada Andino, Jose Daniel, "Extraction and Biochemical Characterization of Alligator mississippiensis glycosaminoglycans and an Ex-vivo Murine Pilot Study to Test their Potential Effect on a Selected Panel of Genes Associated with Cystic Fibrosis" (2016). LSU Doctoral Dissertations. 1245. https://digitalcommo.*

C. Boeriu and others, "Production methods for hyaluronan," *Intl. J. Carb. Chem.*, vol. 2013, article ID 624967 (2013).
B. Blumberg and others, "The effects of proteolytic enzymes on the hyaluronic acid complex of ox synovial fluid," *Biochem. J.*, vol. 66, p. 342 (1957).
E. Ürgeová and others, "Comparison of enzymatic hydrolysis of polysaccharides from eggshells membranes," *Nova Biotec. Et Chim.* 15-2, p. 133 (2016).
M. Khanmohammadi and others, "Sequential optimization strategy for hyaluronic acid extraction from eggshell and its partial characterization," *J. Indus. Eng. Chem.*, vol. 20, p. 4371-4376 (2014).
W. Garnjanagoonchorn and others, "Determination of chondroitin sulfate from different sources of cartilage," *Chem. Eng. Proc.*, vol. 46, pp. 465-471 (2007).
D. Kang and others, "Extraction of hyaluronic acid from rooster comb and characterization using flow field-flow fractionation coupled with multiangle light scattering," *J. Sep. Sci.*, vol. 33, pp. 3530-3536 (2010).
P. Srisantisaeng and others, "Proteolytic activity from chicken intestine and pancreas: extraction, partial characterization and application for hyaluronic acid separation from chicken comb," *J. Sci. Food Agric.*, vol. 93, pp. 3390-3394 (2013).
S. Kulkarni and others, "Extraction, purification and characterization of hyaluronic acid from rooster comb," *J. Appl. Nat. Sci.*, vol. 10, pp. 313-315 (2018).
G. Soares, *Hyaluronic Acid and Collagen Extraction from Chicken Combs*, Masters Thesis (Abstract), Universidade Catolica Portuguesa (2017).
C. Panagos and others, "Characterisation of hyaluronic acid and chondroitin/dermatan sulfate from the lumpsucker fish, *C. lumpus*," *Carb. Polym.*, vol. 106, pp. 25-33 (2014).
P. Kittiphattanabawon, "Characterization of acid-soluble collagen from skin and bone of bigeye snapper (*Priacanthus tayenus*)," *Food Chem.*, vol. 89, pp. 363-372 (2005).
M. Cesaretti and others, "A 96-well assay for uronic acid carbazole reaction," *Carb. Polym.*, vol. 54, pp. 59-61 (2003).
M. Ogawa and others, "Biochemical properties of black drum and sheepshead seabream skin collagen," *J. Agric. Food Chem.*, vol. 51, pp. 8088-8092 (2003).
C. Severo da Rosa and others, "Purification and characterization of hyaluronic acid from chicken combs," *Ciência Rural*, vol. 42, pp. 1682-1687 (2012).
M. Murado and others, "Optimization of extraction and purification process of hyaluronic acid from fish eyeball," *Food Bioproducts Proc.*, vol. 90, pp. 491-498 (2012).

* cited by examiner

*Primary Examiner* — Terry A McKelvey
*Assistant Examiner* — Catheryne Chen
(74) *Attorney, Agent, or Firm* — John H. Runnels

(57) ABSTRACT

Glycosaminoglycans, particularly hyaluronic acid, are extracted from alligator carcasses, feet, backstraps, and eyeballs. The alligator-derived glycosaminoglycans can be used in treatments for cystic fibrosis (CF), in treating other inflammatory conditions, and for other purposes.

5 Claims, 2 Drawing Sheets

GLYCOSAMINOGLYCANS FROM *ALLIGATOR MISSISSIPPIENSIS*

This application is a continuation-in-part of co-pending application Ser. No. 16/223,908, filed Dec. 18, 2018, now abandoned; which claimed the benefit under 35 U.S.C. § 119(e) of the Jan. 2, 2018 filing date of U.S. provisional patent application Ser. No. 62/612,772. The complete disclosures of both priority applications are hereby incorporated by reference in their entirety.

This invention pertains to glycosaminoglycans from the American alligator, *Alligator mississippiensis*, methods of extracting glycosaminoglycans from the alligator, and methods of using the glycosaminoglycans.

BACKGROUND ART

The state of Louisiana has the largest alligator (*Alligator mississippiensis*) industry in the United States. Over 350,000 farm-raised and wild alligators are harvested yearly through a world-renowned sustainable system managed by the Louisiana Department of Wildlife and Fisheries. This system generates significant revenue, and helps protect wetland habitats. After processing slaughtered alligators for skin and meat, the waste is currently disposed in landfills or marketed at very low prices. These by-products contain valuable anti-inflammatory glycosaminoglycans (GAGs) that could potentially be extracted.

CF is a severely life-shortening genetic disorder that globally affects around 70,000 individuals, primarily people of Caucasian descent. Mutations in both copies of the CF transmembrane conductance regulator (CFTR) gene disrupt normal production of the CFTR protein, a chloride channel expressed in the epithelium of several organs including the lungs. A defective CFTR results in the abnormal transport of chloride and sodium across cell membranes, which leads to obstructive lung disease and high morbidity. Early CF symptoms include dysregulated inflammation in the airways, which has been associated with increased levels of pro-inflammatory cytokines and enzymes. The inflammatory response in CF patients is disproportionately high compared to patients without CF, both with and without bacterial infection. Upregulation of nuclear factor kappa beta (NF-κβ) increases the production of interleukin-8 (IL-8) and tumor necrosis factor alpha (TNF-α), which in turn mediate neutrophil activity and the secretion of neutrophil elastase (NE), a serine protease that is involved with bacterial phagocytosis, but that can also degrade airway tissues and cause lung damage. Anti-inflammatory treatments with corticosteroids and high-dose ibuprofen have shown benefits; however, side-effects limit the chronic use of these compounds. TGAse catalyzes cross-linking and deamidation of target proteins in the presence or absence of $Ca^{2+}$. Innate increased oxidative stress in CF airway epithelia induces TGAse up-regulation. TGAse is thus a potential target enzyme for reducing lung inflammation and injury in CF.

Hyaluronic acid (HA) is a natural component of the respiratory system that has been safely used in European CF Centers to improve tolerance to hypertonic saline. HA has also been tested in treating bacterial rhinosinusitis in combination with tobramycin. Globally, the HA market is estimated to be over U.S. $1,000,000,000 annually in the biomedical (e.g., knee osteoarthritis, ophthalmic procedures, and dermal fillers), cosmetics, and food industries. HA, either alone or in the presence of other GAGs, may aid in the down-regulation of chronic and uncontrolled pro-inflammatory responses in CF by reducing the expression of potent cytokines and TGAse.

HA is a linear, negatively charged, highly hydrophilic and non-sulfated GAG. HA is found mainly in the extracellular matrix (ECM) as a sodium salt. This high molecular weight (HMW) GAG, which is degraded by hyaluronidases (HAases), chondroitinases (ChrAses) and reactive oxygen species (ROS), has multiple size-dependent signaling properties. Larger HA chains have anti-inflammatory properties, and smaller ones have pro-inflammatory activity, however the dividing line between the two is not clearly known. HA fragments of 6-12 disaccharides have been reported to significantly increase the expression of inflammatory cytokines and tissue degrading enzymes such as matrix metalloproteinases (MMP). In the airways, HA interacts with a variety of cell surface receptors and HA-binding proteins, to activate intracellular events through various pathways. Inflammation in cystic fibrosis (CF) in mouse airways has been reduced by nebulized HA, as assayed by reductions in TNF-α, myeloperoxidase activity, ROS, and tissue transglutaminase (TGAse) activity. Dose-dependent inhibition of human-NE-induced airway responses has been reported in sheep pretreated with 150 or 300 kDa HA. The water-binding properties of HA may increase the elasticity of lung elastic fibers, thus improving pulmonary mechanics, purulent mucus clearance, or both. The abundance of carboxyl groups in HA may also promote $Ca^{2+}$ binding, thus limiting TGAse inflammatory activity in the airways of CF patients.

Alligator Farming

American alligators (*Alligator mississippiensis*) have been used commercially for their leather since the 1800s and their harvest was generally unregulated through the 1900s. This resulted in severely reduced harvests in the 1950s, and a hunting ban from 1962 to 1972. Since 1972, Louisiana alligators have been managed as a commercial, renewable natural resource; and similar programs are in place in other Gulf Coast states. After rebuilding the population in the 1960's, the wild harvest from 1972 through 2014 produced over 975,000 wild skins. Currently, most of the *A. mississippiensis* farming activity occurs in the southeastern United States, and is led by Louisiana. There is a high-end, largely export market for skins, and a less lucrative but still significant, largely domestic market for alligator meat.

Efforts have been made to better understand and increase the profitability of alligator carcasses and by-products. However, little has been reported to date regarding feasible opportunities to use alligator by-products in a profitable and sustainable manner.

Medicinal Properties of Crocodilian Derivatives

Since ancient times, zootherapy has used in treating different illnesses. The folk medicinal use of crocodilians has been documented in Mexico, India, and Nigeria. There have also been more modern investigations into possible therapeutic and bioactive compounds from crocodilians. These reptiles have a low incidence of diseases in the highly contaminated conditions of marshes and swamps, and most of their wounds heal properly and completely. The antimicrobial, amoebicidal, anti-inflammatory and antiviral properties of compounds synthesized by crocodilians may partially explain the evolutionary success of crocodilians while living in wild and farm aquatic environments teeming with bacteria or agricultural residues.

Although the GAG composition of crocodilian eggs has not been reported in detail, the presence of GAGs is known. Abundant GAGs, including HA, has been reported in several components of the chicken egg. In China, crocodile bile is a folk medicine remedy for asthma and allergies. The Chinese have also used crocodile meat to help asthma sufferers, a person getting a cold, and even improve the strength of the lungs, although such claims lack scientific basis. Farmed crocodile tail oil has been evaluated for the treatment of microbial infections and inflammatory conditions. *Staphylococcus aureus, Klebsiella pneumoniae*, and *Candida albicans* are susceptible to 6-15% (w/v) oil preparations. In an induced auricular dema mouse model, oral administration and topical application of crocodile oil have produced anti-inflammatory effects. Functional properties have been attributed to collagen and gelatin from different animal sources.

It has been observed that American alligators *A. mississippiensis* often sustain serious injuries in territorial disputes with other alligators. However, the reptiles exhibit a remarkable ability to heal rapidly and without infection. Several studies suggest that alligators have evolved a complex innate immune system.

Hyaluronic Acid and Sulfated Glycosaminoglycans

Classification and Structures

GAGs are large heteropolysaccharides comprising repeating disaccharide units. GAGs are made of an amino sugar, typically N-acetylglucosamine (GlcNAc) or N-acetylgalactosamine (GalNAc), and a uronic acid, typically glucuronic acid (GlcA). There are two main types of GAGs. Sulfated GAGs include heparan sulfate (HS), in which heparin (HP) is highly sulfated, based on D-GlcNAc and D-GlcA or iduronic acid (IdA). Chondroitin sulfate (CS) is based on D-GalNAc and D-GlcA. Dermatan sulfate (DS) comprises D-GalNAc and L-IdA. Keratan sulfate (KS) is the most heterogeneous GAG, and is based on D-GalNAc and D-galactose. The non-sulfated GAGs include hyaluronan, also called sodium hyaluronate or HA, comprising D-GlcNAc and D-GlcA bound through $\beta 1,4$ and $\beta 1,3$ glycosidic bonds. HA is the principal non-proteinaceous component of ECM, and consequently the most abundant GAG in alligator by-products.

Biosynthesis

HA is ubiquitously expressed in animal ECM. Unlike sulfated GAGs that are produced in the Golgi apparatus, HA is synthesized at the inner face of the plasma membrane as a free linear polymer not anchored to any proteins. It is synthesized by three transmembrane glycosyl-transferases or HA synthases (HAS1, HAS2, and HAS3). Although these isozymes synthesize essentially the same type of HA molecule, they have distinct stabilities, elongation rates for the growing HA chain, and Km values. HAS2 is the main HA synthetic enzyme in adult cells. HAS2 generates HA with a large and broad molecular weight distribution (>2000 kDa, a degree of polymerization around 5,000 disaccharides). Shorter chains tend to be produced by HAS1 (200-2000 kDa) and HAS3 (100-1000 kDa).

There is no consensus in the literature for the nomenclature of HA with different molecular weights. Here we shall use the nomenclature: high molecular weight HA (HMW-HA), above 1000 kDa; medium molecular weight HA (MMW-HA), 250-1000 kDa; low molecular weight (LMW-HA), 10-250 kDa; and oligosaccharides (oHA), below 10 kDa.

HA is usually found in synovial fluid, vitreous humor and connective tissue. Sulfated GAGs are smaller on average than HA, with sizes ranging from 4-70 kDa. CS has a molecular weight of 5-50 kDa and is found in cartilage, tendon, ligaments, and arteries. DS (15-40 kDa) is found in skin, blood vessels and heart valves. KS (4-19 kDa) is found in the cornea and in cartilage, typically aggregated with CS. HP (10-12 kDa) is a naturally occurring anticoagulant stored in mast cell vesicles especially in the liver, lungs and skin. HS (10-70 kDa) is ubiquitously expressed on animal cell surfaces.

Signaling and Biological Functions of Hyaluronan

Even with their simple structures, GAGs fulfill several distinct functions. In some cases there are opposing, size-dependent functions. HA contributes not only to the structural and physiological characteristics of tissues, but also mediates cell behavior during morphogenesis, tissue remodeling, inflammation and diseases. As a signaling molecule, HA interacts with a variety of cell surface receptors to activate intracellular events. HA is the main ligand for CD44, a receptor expressed on the surface of almost all human cells, that is involved in many cell-cell interactions and in a wide variety of cellular functions. CD44 plays a critical role in HA clearance and homeostasis following lung injury, influencing recovery from pulmonary inflammation. It has been reported that mice accumulate LMW-HA following bleomycin-induced lung injury; however, after inflammation is resolved, HMW-HA synthesis predominates. LMW-HA levels in the bronchoalveolar lavage (BAL) of CD44-negative mice have been reported to be twice that seen in wild-type mice. HA fragments induce pro-inflammatory macrophage inflammatory protein-2 (MIP-2), the murine equivalent to human IL-8. Lung epithelial cell-specific overexpression of HMW-HA appear to be protective against lung injury. Mice and macrophages exposed to HMW-HA prior to LPS injection had greatly decreased interleukin-6 (IL-6) and TNF-$\alpha$ levels in serum and mRNA expression, respectively. This effect was not observed in CD44-negative mice or macrophages. HA can modulate key cancer cell functions through interaction with its CD44 and receptor for hyaluronan-mediated motility (RHAMM) receptors.

The interaction of HA with RHAMM can trigger several signaling cascades including the NF-$\kappa\beta$ pathway. RHAMM is normally localized intracellularly, and is only released by some poorly defined stimuli. Extracellularly, RHAMM associates with CD44; and upon binding with HA it activates intracellular signaling pathways. The interaction of RHAMM with an oHA (6-mer) plays a role in the inflammatory and fibrotic processes resulting from acute lung injury by bleomycin in mice. A study using primary tracheal epithelial cell cultures treated with HA (200 kDa) at 50 μg/mL suggested HA serves a key role in mucosal host defense. HA, through its interaction with RHAMM, stimulates ciliary beating and hence the clearance of foreign material from mucosal surfaces while still regulating enzyme (lactoperoxidase and tissue kallikrein) homeostasis.

Toll-like receptors (TLRs) are able to rapidly initiate the innate immune response, which represents the first defense against pathogens. In a murine lung injury model, the knockout of TLR2 and TLR4 abolished completely the activation of chemokines in macrophages. Moreover, oHA induced the nuclear translocation of NF-$\kappa\beta$ and production of TNF-$\alpha$. The expression of MMP-2 and IL-8 is also stimulated by HA fragments, in part by signaling of TLR4. On the other hand in human monocytes, HMW-HA via its engagement with CD44 and TLR4 is a positive regulator of IL-1R-associated kinase-M (IRAK), which is thought to be a negative regulator of inflammatory TLR signaling. HA of different sizes can also signal through the lymphatic vessel endothelial hyaluronan receptor 1 (LYVE 1) and the hyaluronan receptor for endocytosis (HARE). HARE has a complex structure including several HA and other GAG binding motifs. The binding of human or rat HARE with HA (optimal size 140 kDa) has been shown to stimulate the activation of NF-κβ. In aggregate, affinity for receptors, receptor clustering and uptake differs depending on HA size, which may affect downstream signaling cascades. Cell type may affect differences in HA signaling.

Binding of HA with tumor necrosis factor-alpha stimulated gene-6 (TSG-6) is involved in the mediation of lymphocyte migration during inflammation. This binding results in the formation of fibrils that adhere to lymphocytes, preventing direct contact between inflammation promoting receptors or elastases and the underlying tissues. HA "cables" synthesized by mouse or human airway smooth muscle cells can also form independently, in the absence of TSG-6. These cables are capable of binding a large number of leukocytes and can sequester pro-inflammatory chemokines through interactions with CS and DS chains.

An investigation on airway responses in sheep showed that the preventive inhibitory effects of inhaled HA (3, 6, 7 or 15 mg in 3 ml phosphate buffered saline (PBS)) against human NE-induced bronchoconstriction could extend for at least 8 hours. Both LMW-HA and MMW-HA showed a dose-dependent inhibition of the inflammatory response. Above 150 kDa, molecular weight seemed to be less of a factor, and effective protection depended primarily on the dose. It has been proposed that this protective effect of HA may be accompanied by an improvement in pulmonary mechanics, due to HA's ability to retain water, which may help increase the elasticity of lung elastic fibers. Binding of HA to alveolar septal elastic fibers following intratracheal administration may inhibit degradation of the fibers by elastases. Furthermore, lipopolysaccharide-induced TNF-α, IL-6, and interleukin-1 beta (IL-1β) in human macrophages have been dose-dependently suppressed by 2,700 kDa HA (0.01, 0.1 and 1 mg/ml); by contrast, HA (800 kDa) showed no significant effect even at 3 mg/ml. It has been proposed that HA could be injected into arthritis joints as an anti NF-κβ agent.

Due to its biocompatibility, biodegradability, non-immunogenicity, water binding properties and receptors (e.g., receptors CD44, RHAMM, TSG-6, HARE, and LYVE 1), HA has drawn attention in biopharmaceutics. HA-drug conjugates may be used to increase the solubility, permeability and bioavailability of anti-cancer, anti-inflammatory, and other drugs.

CS exhibits anti-inflammatory activity in osteoarthritis. CS or its disaccharides reduce inflammation (TNF-α, IL-1β, ROS and nitric oxide) in joint chondrocytes and synovial membrane through the inhibition of NF-κβ nuclear translocation. CS may play a role in synovial angiogenesis. Synovial biopsies from inflamed areas expressed pro-angiogenic phenotypes promoted by IL-1β, and CS reverses this effect in a dose-dependent manner. In a psoriasis model using normal human keratinocytes, CS downregulates the NF-κβ and signal transducer and activator of transcription 3 (STAT3) pathways. These effects limit the release of key psoriatic pro-inflammatory cytokines such as TNF-α, IL-8, IL-6 and the cutaneous T cell-attracting chemokine (CCL27). HA, CS and DS extracted from fish have been shown to reduce gliadin-mediated inflammation in a celiac disease model using human Caco-2 cells, through a decrease in the production of IL-1β. Octasaccharides of over-sulfated CS can inhibit herpes simplex virus infections, and a specific CS sequence could be a potential target for the treatment of malaria. Highly sulfated CS and DS bind strongly to key liver regeneration growth. Tissue regeneration properties in the central nervous system have also been attributed to CS disaccharides. Cisplatin-CS liposomes are avidly internalized by highly metastatic liver cancer cells, inducing cell death. It has also been reported that sulfated GAG-rich wound fluids inhibit the antibacterial action of the antibacterial peptide LL-37 through specific GAG-LL-37 hydrophobic interactions and hydrogen bonding. HA and sulfated GAGs might also be therapeutic agents in other diseases with strong inflammatory components, such as inflammatory bowel disease, atherosclerosis, Parkinson's and Alzheimer's diseases, multiple sclerosis, lupus, rheumatoid arthritis and CF.

Degradation

HAses and ROS degrade HA, and more so with aging and during certain. HAases fall into three general classes. The first class constitutes a family of enzymes derived from animal venoms, urine, blood, and sperm, among others. They are responsible for fragmenting HA of all sizes into short chains, down to tetra-saccharides. The second class of HAases has not been extensively studied; they are known as the "leech HAases" due to their presence in blood-sucking organisms such as leeches, bed bugs, ticks, flies, mosquitoes, and certain crustaceans. Microbial HAases are the third type; these increase the permeability of the ECM to facilitate invasion of pathogens and the spread of toxins. Fungal HAases have not been characterized yet.

Higher levels of HAase expression and activity occur during some diseases. A type 1 HAase has been shown to have an important regulatory role in bladder cancer; increases in its relative abundance can promote tumor growth and proliferation. HAases may be involved in the turnover of HA during early phases of lung injury, and may be involved in lung fibrosis. Acute exacerbations of chronic obstructive pulmonary disease (COPD) are associated with increased HAase activity in BAL, which may contribute to airway inflammation and decline in lung function.

The molecular weight of HA may be altered by oxidative damage. Average molecular weight decreases in mice exposed to cigarette smoke (decrease ~70 kDa). Hydroxides are at least partly responsible for HA degradation. Inhibition of ROS-induced HA degradation correlates to reduced inflammation in bleomycin- and asbestos-induced models of pulmonary fibrosis. In a murine model of allergic contact dermatitis, increased production of ROS is accompanied by HA breakdown into pro-inflammatory, LMW fragments in the skin. Non-enzymatic reactions that may degrade HA include those with (or induced by) acidity, alkalinity, ultrasound, and heat.

Sources

GAGs have a variety of structures and functions that vary depending on such factors as their source, type of tissue, age, physiological conditions and extraction methods. This heterogeneity complicates the reproducibility of results.

BMW-HA has been extracted from fresh cattle vitreous humor with a reported yield of 0.25 g from 100 eyes. A common source of HA today is chicken combs, which can yield about 15 μg hexuronic acid/mg dry tissue for 42-day-old animals, or about 2.4 μg hexuronic acid/mg wet chicken combs. Total GAGs can be extracted by acetone dehydration, followed by choloroform:methanol delipidation, and then papain digestion, and precipitation by a series of NaCl and ethanol washes. Higher yields have been reported from rooster combs in 52-week-old animals (4.0 μg uronic acid/mg wet tissue) following an extraction method in which samples were dehydrated with acetone prior to papain digestion, trichloroacetic acid (TCA) deproteinization and dialysis. HA concentration in rooster combs has been estimated to be about twice as high as that in the wattle. HA has also been extracted from rooster in a larger-scale process, in which frozen comb samples (500 g) were ground and defatted/dehydrated with acetone to yield 80 g of dry material; that was then extracted with sodium acetate and purified with ethanol, followed by dialysis; finally, the HA was precipitated with ethanol and heat-treated to yield 1 µg dry HA/mg wet tissue, with an average molecular weight of 1200 kDa. HA has also been derived from pig synovial fluid (0.5-6 g HA/L), and pig vitreous humor (0.04 g HA/kg.

Fish and fish eyeballs are also a source of HA GAGs. Swordfish (*Xiphias gladius*) and shark (*Prionace* sp.) vitreous humor can be decomposed and clarified by centrifugation before ultrafiltration, electrodeposition and alcoholic precipitation to yield 0.055 and 0.3 g HA/kg of vitreous humor from swordfish and shark, respectively. GAGs have also been isolated from haddock (*Theragra chalcogramma*) by papain digestion, TCA deproteinization, dialysis, and cetylpyridinium chloride (CPC) precipitation. Fourier transform infrared (FT-IR) absorption spectra of the purified haddock extracts fit the main characteristics of GAGs and suggested the presence of CS and DS, but mainly HA. Chicken (42 d old) keel cartilage has been reported to be a good source of CS following extraction with magnesium chloride. Results showed a yield of 33 mg GAGs/g wet keel cartilage; 75.5% of the GAGs were CS, with an average molecular weight of 48.5 kDa.

Despite available animal sources for HA, most commercial production today is based on microbial fermentation due to its lower costs and environmental impact. Culture conditions (e.g., pH, temperature, culture media, agitation speed, shear stress, dissolved oxygen, bioreactor type) and production modes (batch vs continuous) have been extensively studied to enhance microbial HA yields. *Streptococcus* sp. is the main producer, however the industry is facing issues due to its pathogenicity. Recently, the production of HA by *Streptococcus equi* subsp *zooepidemicus* in media formulated from fish by-products was investigated. The process yielded more than 2 g HA per liter with a molecular weight of 1730-1900 kDa at a competitive cost.

HA has also been produced by *Bacillus subtilis* using a water-based process and a growth medium free of animal ingredients or toxins. Other bacteria used for recombinant HA production have included *Lactococcus lactis, Agrobacterium* sp., and *E. coli*. Recombinant HA production yields are generally lower than bacterial fermentation yields.

C. Boeriu and others, "Production methods for hyaluronan," *Intl. J. Carb. Chem.*, Vol. 2013, article ID 624967 (2013) is a review article providing an overview of methods that have been used to produce hyaluronic acid.

B. Blumberg and others, "The effects of proteolytic enzymes on the hyaluronic acid complex of ox synovial fluid," *Biochem. J.*, vol. 66, p. 342 (1957) discloses the use of a proteinase to separate hyaluronic acid from a proteinaceous complex derived from ox synovial fluid.

E. Ürgeová and others, "Comparison of enzymatic hydrolysis of polysaccharides from eggshells membranes," *Nova Biotech. Et Chim.* 15-2, p. 133 (2016) disclosed the isolation of hyaluronic acid from eggshell membranes by enzymatic hydrolysis using pepsin.

M. Khanmohammadi and others, "Sequential optimization strategy for hyaluronic acid extraction from eggshell and its partial characterization," *J. Indus. Eng. Chem.*, vol. 20, pp. 4371-4376 (2014) discloses processes for extracting hyaluronic acid from eggshell, varying parameters of the process (e.g., pH, temperature) to optimize the extraction procedure.

W. Garnjanagoonchorn and others, "Determination of chondroitin sulfate from different sources of cartilage," *Chem. Eng. Proc.*, vol. 46, pp. 465-471 (2007) discloses the extraction of chondroitin sulfate from shark fin, ray cartilage, crocodile cartilage, and chicken keel via a method whose steps included (among others) enzymatic hydrolysis, acidic solubilization, centrifugation, and precipitation.

D. Kang and others, "Extraction of hyaluronic acid from rooster comb and characterization using flow field-flow fractionation coupled with multiangle light scattering," *J. Sep. Sci.*, vol. 33, pp. 3530-3536 (2010) discloses the extraction of hyaluronic acid from rooster combs via a method whose steps included (among others) solvent extraction, precipitation, and centrifugation.

P. Srisantisaeng and others, "Proteolytic activity from chicken intestine and pancreas: extraction, partial characterization and application for hyaluronic acid separation from chicken comb," *J. Sci. Food Agric.*, vol. 93, pp. 3390-3394 (2013) disclosed the use of protease extracted from chicken intestine and chicken pancreas to digest chicken combs, as part of a process to extract hyaluronic acid from the chicken combs.

S. Kulkarni and others, "Extraction, purification and characterization of hyaluronic acid from rooster comb," *J. Appl. Nat. Sci.*, vol. 10, pp. 313-315 (2018) discloses the extraction of hyaluronic acid from rooster comb, via a method whose steps included (among others) solvent extraction, precipitation, and centrifugation.

G. Soares, *Hyaluronic Acid and Collagen Extraction from Chicken Combs*, Masters Thesis (Abstract), Universidade Catolica Portuguesa (2017) discloses a conjoint extraction of hyaluronic acid and collagen from chicken combs.

C. Panagos and others, "Characterisation of hyaluronic acid and chondroitin/dermatan sulfate from the lumpsucker fish, *C. lumpus,*" *Carb. Polym.*, vol. 106, pp. 25-33 (2014) disclosed that the lumpsucker, *Cyclopterus lumpus*, a cottoid teleost fish found in the cold waters of the North Atlantic and North Pacific, is a possible source of glycosaminoglycans. A method for extracting glycosaminoglycans from the lumpfish was disclosed, a method that included steps of proteolytic digestion and anion exchange.

P. Kittiphattanabawon, "Characterization of acid-soluble collagen from skin and bone of bigeye snapper (*Priacanthus tayenus*)," *Food Chem.*, vol. 89, pp. 363-372 (2005) discloses the extraction of acid-soluble collagens from the skin and bones of the bigeye snapper, *Priacanthus tayenus*.

M. Cesaretti and others, "A 96-well assay for uronic acid carbazole reaction," *Carb. Polym.*, vol. 54, pp. 59-61 (2003) discloses a sensitive and reproducible 96-well assay for uronic acid-bearing polyanions such as hyaluronic acid, chondroitin sulfate, dermatan sulfate, and heparin.

M. Ogawa and others, "Biochemical properties of black drum and sheepshead seabream skin collagen," *J. Agric. Food Chem.*, vol. 51, pp. 8088-8092 (2003) reported the isolation of acid-soluble collagen and pepsin-solubilized collagen from skins of the fishes *Pogonias cromis* and *Archosargus probatocephalus*

C. Severo da Rosa and others, "Purification and characterization of hyaluronic acid from chicken combs," *Ciência Rural*, vol. 42, pp. 1682-1687 (2012) discloses a process for obtaining hyaluronic acid from chicken combs by a process that involved dehydration and delipidation in acetone, delipidation in chlorofom:methanol, enzymatic digestion, centrifugation, and precipitation in ethanol.

M. Murado and others, "Optimization of extraction and purification process of hyaluronic acid from fish eyeball," *Food Bioproducts Proc.*, vol. 90, pp. 491-498 (2012) discloses a process for extracting HA from the vitreous humour of fish, with successive steps of: protein electrodeposition, selective recovery in hydroalcoholic solution of impure sediments obtained by alcoholic exhaustive precipitation, alkaline treatment to precipitate HA and solubilize proteins, and HA recovery by alkaline suspension of the precipitate in hydroalcoholic phosphate monosodium.

U.S. Pat. No. 7,109,300 discloses a process for extracting collagen from calcified tissues such as fish skin with scales, alligator skeletons, and crustacean exoskeletons.

Cystic Fibrosis

Introduction

CF is a life-limiting condition that affects 29,000 individuals in the United States and 70,000 worldwide, with an estimated frequency of 1 in 2,500 births. The disease affects primarily those of European descent, but it has been reported in all races and ethnicities. It is an autosomal recessive disorder specifically related to abnormalities in the expression and function of the CFTR resulting in abnormal ion transport across epithelial surfaces in the sweat glands, and gastrointestinal, reproductive and respiratory systems. Abnormal salt and water transport results in viscous secretions both in the airways of the lungs and in pancreatic ducts, leading to obstructions that cause inflammation, tissue damage, and finally failure of organ systems. Obstructive lung disease is the primary cause of morbidity, and is responsible for ~80% of mortality. The median survival age for CF patients in the United States was 40.7 years in 2013 with the use of currently available therapies (pancreatic enzyme supplements, antibiotics, anti-inflammatory drugs and sputum thinners, and CFTR potentiators).

The Cystic Fibrosis Transmembrane Conductance Regulator Protein

CFTR is a member of the adenosine triphosphate (ATP)-binding cassette family of transporters, which use energy from ATP hydrolysis to pump substrates across cellular membranes. It is the major epithelial ion (Cl−) regulator, located primarily in the apical plasma membrane. It is important in transepithelial salt transport and fluid flow. The CFTR protein has five domains: two membrane-spanning domains (MSD-1 & MSD-2), two nucleotide-binding domains (NBD-1 & NBD-2), and a regulatory domain (RD). Opening the anion pathway in CFTR requires phosphorylation of the channel by cyclic adenosine monophosphate-dependent protein kinase A (cAMP-PKA). Once the CFTR RD is phosphorylated, channel gating is regulated by ATP hydrolysis in the NBDs. The RD is dephosphorylated by protein phosphatases to return the channel to its inactive state. CFTR function is regulated by nucleotide binding and phosphorylation, and the amount and quality of CFTR production are also regulated in the endoplasmic reticulum.

The CFTR is directly responsible for CF. A person must have two abnormal CFTR genes to manifest the disease. According to the CFTR Mutation Database (http://www-.genet.sickkids.on.ca/), there are six classes of CFTR mutations, which include 2,006 different mutations that can result in a particular phenotype.

For example, the F508del mutation is associated with severe CF. It is the most common mutation, occurring in ~86.4% of CF patients in one or both alleles. F508del is a class II mutation, in which the CFTR protein is expressed but misfolded, keeping it from reaching the cell surface, due to a phenylalanine residue deletion in the 508 position. Other CFTR mutation classes include nonsense mutations (Class I), altered gating mutations despite expression of full length protein (Class III), missense mutations resulting in lowered Cl− permeability (Class IV), insufficient synthesis of CFTR (Class V), and mutations leading to reduced CFTR half-life in the apical membrane (Class VI). These dysfunctions in the CFTR disrupt ion transport in the epithelia of various organs, which results in many manifestations of the disease, from airway disease and pancreatic failure to male infertility and elevated electrolyte levels in sweat.

In addition to its role in Cl− transport, the CFTR active state negatively regulates the epithelial Na+ channel (ENaC). Since Cl− conductance is defective in CF, ENaC currents are not inhibited, resulting in increased Na+ absorption in the airway epithelium and depletion of the airway surface liquid (ASL), also called the "low-volume hypothesis."

Airway Pathophysiology in Cystic Fibrosis

Abnormal CFTR expression in the human bronchus affects predominantly the submucosal glands. Clinicians often describe CF as a vicious cycle of airway inflammation, obstruction, and infection in which each of these components contributes to the progression of the lung disease. The main cause of death is chronic inflammation and persistent infections with *Pseudomonas aeruginosa* and other pathogens. This section focuses only the pulmonary aspects of this disease and does not address other important aspects of this illness including gastrointestinal, endocrine and metabolic manifestations.

CF leads to severe pathological changes in the airway epithelium as it induces an early, intense and constitutive inflammatory process even before the onset of bacterial infection. A congenital pro-inflammatory phenotype is caused by an innate increase in ROS, promoted by misfolded protein stress and TGAse-driven defective autophagy of misfolded or damaged CFTR aggresomes. TGAse is a driver of inflammation in CF airways. TGAse can be upregulated by ROS. This inflammatory process leads to the increased expression of NF-κβ and pro-inflammatory cytokines as well as a large recruitment of neutrophils. Excessive production of the serine protease NE overwhelms normal anti-proteinase capacity and results in irreversible airway structural damage, which in turn overwhelms normal repair pathways. Although NE's physiological role is to degrade phagocytosed proteins, it also degrades structural proteins such as elastin, collagen, fibronectin and proteoglycans, causing damage to the airway epithelia and contributing to bronchiectasis progression. NE is also the most significant predictor of bronchiectasis in early-life CF. Neutrophils from CF patients release significantly more ROS than neutrophils from healthy individuals, thus magnifying the inflammatory response. Furthermore, the lysis of neutrophils releases large amounts of DNA that contribute to the increased viscosity and adhesiveness of lung secretions and to the formation of mucous plugs.

The airway tissue damage and the ion transport defects in CF epithelia cause deficiencies in mucociliary clearance (MCC) that result in airway obstruction. Sodium hyperabsorption and defective chloride secretion drive increased water absorption by osmosis, which both reduces mucus clearance and increases mucus adherence, resulting in reduced ASL height. The ASL comprises two layers above the epithelial surface: a mucus layer and a perciliary liquid layer. It has been suggested in mouse, human and in vitro studies that the hydration status of the ASL predicts the outcome of therapeutic interventions. Understanding this pathological condition is critical, as MCC is a primary physiological defense mechanism. MCC is used as an outcome measure in assessing the effectiveness of physical and pharmacological therapies. Normal MCC requires intact airway epithelial cells, but those cells are compromised in CF airways due to exaggerated expression of NE. In vitro mucus transport is lost within 24 h in CF cultures, compared to up to 72 h in normal airways, mainly as a result of increased absorption of liquid from the culture surface. A study in mice with airway-specific overexpression of ENaC demonstrated that the lungs were normal at birth, but early surface dehydration occurred, along with increased mucus concentration and increased mucus adhesion, producing mucus plugging that triggers airway inflammation and is associated with early mortality. In humans, large volumes of viscous mucopurulent sputum accumulate, putting patients at a higher risk for lung infections. Regular administration of hypertonic saline solution may provide some benefit. Decreased lung function and COPD continue to be the leading causes of CF morbidity and mortality.

Chronic infections are also a serious problem for most CF individuals. Paradoxically, the large numbers of neutrophils present in CF airways fail to effectively kill colonizing bacteria. Bactericidal activity has been reported in CF epithelia at low NaCl concentrations. The CF ASL has a high NaCl concentration, which reduces bactericidal activity. Deficiency in $HCO_3$-transport may also play a role. CFTR facilitates HCO3-secretion. The absence or malfunction of CFTR causes the ASL pH to fall, which inhibits antimicrobial function, reduces MCC, and facilitates bacterial colonization. Midkine has been seen at 100-fold higher levels in CF sputum as compared with sputum from healthy control subjects. It degrades into smaller fractions by NE, impairing its bactericidal properties. Increased salt and acidity also impaired its bactericidal properties in vitro.

Bacterial infections tend to vary with the CF patient's age. Early infections are typically *Staphylococcus aureus, P. aeruginosa,* and *Haemophilus influenzae.* In older patients *P. aeruginosa* is by far the most significant pathogen. There is evidence indicating that in young children with CF, early *P. aeruginosa* infection induces a gradual decline in lung function and a gradual increase in morbidity. *Pseudomonas* can play a critical role when a patient's overall health is otherwise moderately to severely compromised. Even though the prevalence of *P. aeruginosa* continues to decrease due to prevention of initial infection, there is still a prevalence of multi-drug resistant *P. aeruginosa* (18.1% of CF patients in 2014). A five-fold increase in prevalence of methicillin-resistant *S. aureus* has also been reported. *S. aureus* co-infection increases the risk of an initial *P. aeruginosa* infection in young CF patients.

In CF patients *P. aeruginosa* has demonstrated a very high level of adaptation and mutability to establish a persistent infection, likely caused by a diversity of infecting organisms, ineffective host defenses, and ongoing antibiotic therapies.

Among pathogens that have been identified later in the course of CF disease are the *Burkholderia cepacia* complex, Strenotrophomonas *maltophilia, Achromobacter, Aspergillus* and other non-tuberculous mycobacteria. Of these, the *B. cepacia* complex is the most dangerous because of its rapid progression to death through high fevers and bacteremia.

Current Treatments

Current CF clinical practice guidelines recommend that patients aged 6 and older visit care centers at least four times per year to conduct microbial cultures, perform pulmonary function tests, receive an influenza vaccine, and measure liver enzyme levels and blood levels of fat-soluble vitamins. CF typically requires more intensive treatments as the disease progresses, and therefore the availability of multiple pulmonary therapies is beneficial. Typically, chronic pulmonary therapies use dornase alfa, hypertonic saline, ibuprofen, tobramycin, or other preparations. In the United States the mean annual cost of care for CF patients with mild impairment in lung function is over $43,000. These costs are driven primarily by medications, but also include hospitalization costs, emergency room and home nursing visits and indirect costs associated with missed school or work days. Typical costs of care are comparable in other developed countries.

Dornase alpha is an "orphan drug," as a recombinant human deoxyribonuclease (DNase) that hydrolyzes DNA in the sputum, reducing the lung viscosity and improving MCC. The nebulized DNase is currently prescribed for the majority of CF patients in the U.S., in addition to or in lieu of hypertonic saline. Dornase alpha has been reported to improve symptoms of airway inflammation, including neutrophil content, NE activity and IL-8.

Hypertonic saline (HTS) is also available to CF patients as a means to restore ASL. HTS is a solution with an osmotic pressure greater than that of physiologic isotonic NaCl solution (0.9%). Inhaled HTS has been reported to increase airway antioxidant levels, improve MCC, increase ASL hydration, and inhibit ENaC, among other positive effects. In adult CFTR knockout mice, nebulized 7% sterile HTS (2 mL/mouse) promoted an increase in glutathione, an airway antioxidant that can protect the airways from hypochlorous acid mediated injury. A long-term (48 week) clinical study with 164 CF patients found that patients treated with 7% HTS (4 ml twice daily) had significantly higher forced vital capacity (FVC) and FEV1, as well as fewer pulmonary exacerbations than control patients; and had significant improvements in quality of life. HTS at a concentration of 3% or higher has been used to create an osmotic gradient that draws water into the airway surface, therefore improving ASL and facilitating MCC. The inhibition of luminal sodium conductance by HTS may be associated with improved fluid transport across the respiratory epithelium, improved MCC, and increased lung function. There is increasing evidence suggesting that HTS is beneficial through its anti-inflammatory properties, reducing IL-8 concentrations and neutrophil chemotaxis in CF airways. Moreover, HTS has the ability to reduce bacterial activity and biofilm formation. The tolerability and pleasantness of 7% HTS can be significantly improved when administered together with 0.1% HA, thus improving adherence to HTS therapy due to reduced cough, throat irritation and saltiness.

Symptomatic therapies to treat CF patients include non-chronic use of high-dose ibuprofen (25-30 mg/kg). Despite its apparent benefits, ibuprofen is infrequently used due to the need to measure plasma levels and because of the potential renal and gastrointestinal side effects.

Anti-infective pulmonary therapies with inhaled tobramycin, inhaled aztreonam or azithromycin are also used in many CF patients infected with *P. aeruginosa.*

GAGs have been investigated as potential treatments for CF and airway disease symptoms due to their water-retaining, re-epithelizing and anti-inflammatory properties. Nebulized 300-500 kDa HA (0.5 mg HA/animal/day for 7 days) was effective in controlling inflammation in vivo in mice CF airways, as well as in vitro in human airway epithelial cells (100 µg HA/ml for 24 h). Adult sheep treated with nebulized 150 kDa or 300 kDa HA (3-15 mg/ewe), dose-dependently improved pulmonary resistance after challenge with human NE. Moreover, seven days after treatment of cultured ovine tracheal cells with HA, ciliary beat frequency increased by 16%, which may be indicative of the late expression of an HA-binding receptor. Researchers have also proposed a role for HA in mucosal host defense, by stimulating ciliary beating through its interaction with ciliary RHAMM. Intranasal use of sodium hyaluronate (9 mg twice daily for 30 days) in patients undergoing functional endoscopic sinus surgery for nasal polyposis has significantly improved MCC and other important clinical parameters.

The anti-inflammatory and tissue regeneration properties of sulfated GAGs have been reviewed in various diseases, however reported results have not been promising for symptomatic treatment of CF. For example, a pilot clinical study demonstrated no evidence of improved $FEV_1$, MCC or inflammation markers with a dose of 50,000 I.U. of heparin twice daily for two weeks. It has also been shown that high expression of CS and HS in normal and CF human lung tissue facilitate the binding of IL-8, protecting it from proteolysis and prolonging its activity.

SUMMARY OF THE INVENTION

We have discovered a method to extract glycosaminoglycans (GAGs), particularly hyaluronic acid (HA), from alligator carcasses (ACS), feet (AFT), backstraps (ABS), and eyeballs (AEB). The alligator-derived GAGs can be used in treatments for cystic fibrosis (CF), treating inflammation, and other purposes. In a preferred embodiment, materials other than HA are removed sequentially: water soluble proteins are removed, followed by demineralization, then delipidation, then enzymatic hydrolysis of protein, and precipitation of endotoxin-free HA.

In one embodiment, the method comprises the steps of:
(a) preparing a crude aqueous mixture from one or more hyaluronic-acid-containing components from one or more deceased *Alligator mississippiensis* individuals; wherein the one or more components are selected from the group consisting of all or part of the carcass, backstrap, feet, and eyeballs; wherein the crude aqueous mixture comprises at least some of the hyaluronic acid from the one or more components; and wherein the crude aqueous mixture may contain incidental pathogens;
(b) centrifuging the crude aqueous mixture to separate a liquid supernatant from a solid pellet; wherein the majority of the hyaluronic acid from the crude aqueous mixture partitions with the liquid supernatant; and separating the liquid supernatant containing hyaluronic acid from the solid pellet;
(c) hydrolyzing proteins in the liquid supernatant by enzymatic proteolysis following said centrifuging step, or hydrolyzing proteins in the crude aqueous mixture by enzymatic proteolysis before said centrifuging step, or both;
(d) fractionating the proteolyzed liquid supernatant to separate a selected molecular weight range of hyaluronic acid molecules; and
(e) heating the molecular-weight-range-fractionated hyaluronic acid at a temperature and for a time sufficient to inactivate any pathogens admixed with the separated hyaluronic acid molecules.

In one embodiment:
(a) the one or more components comprise vitreous humor from one or more *Alligator mississippiensis* eyeballs;
(b) the crude aqueous mixture is prepared by mixing the vitreous humor with water, and homogenizing the vitreous humor/water mixture;
(c) said hydrolyzing step comprises enzymatic proteolysis of the liquid supernatant following said centrifuging step; and
(d) said fractionating step comprises dialyzing the proteolyzed liquid supernatant against water through a semipermeable membrane.

In one embodiment:
(a) the one or more *Alligator mississippiensis* components are selected from the group consisting of all or part of the carcass, the backstrap, and the feet;
(b) the crude aqueous mixture is prepared by removing any sinews that may be present in the one or more components, or grinding the one or more components, or both; and by bleaching, defatting, and demineralizing; and by mixing with water;
(c) said hydrolyzing step comprises enzymatic proteolysis of the crude aqueous mixture before said centrifuging step;
(d) said fractionating step comprises dialyzing the proteolyzed liquid supernatant against water through a semipermeable membrane;
(e) the method additionally comprises, following said fractionating step, precipitating hyaluronic acid by mixing the dialyzed liquid supernatant with sodium chloride and ethanol;
(f) re-dissolving the precipitated hyaluronic acid in water; and
(g) performing a second centrifuging step on the re-dissolved hyaluronic acid to separate a liquid supernatant from a solid pellet; wherein the majority of the hyaluronic acid partitions with the liquid supernatant.

The novel method for extracting hyaluronic acid is shorter, easier to implement, and more efficient than most methods that have been reported in the literature. The novel method uses smaller quantities of toxic compounds than have most previously-reported methods of isolating HA.

Unlike most previous methods for extracting HA, the novel method does not employ a lengthy extraction time at pH that degrades HA. Many prior methods have degraded HA over the course of the isolation, leading to low yields that are not commercially cost-effective.

The molecular weight of HA isolated using previous methods has been relatively low. The novel method can isolated HA with medium and high molecular weights.

MODES FOR PRACTICING THE INVENTION

Materials and Methods

Experimental Design and Statistical Analysis

Figure 1:
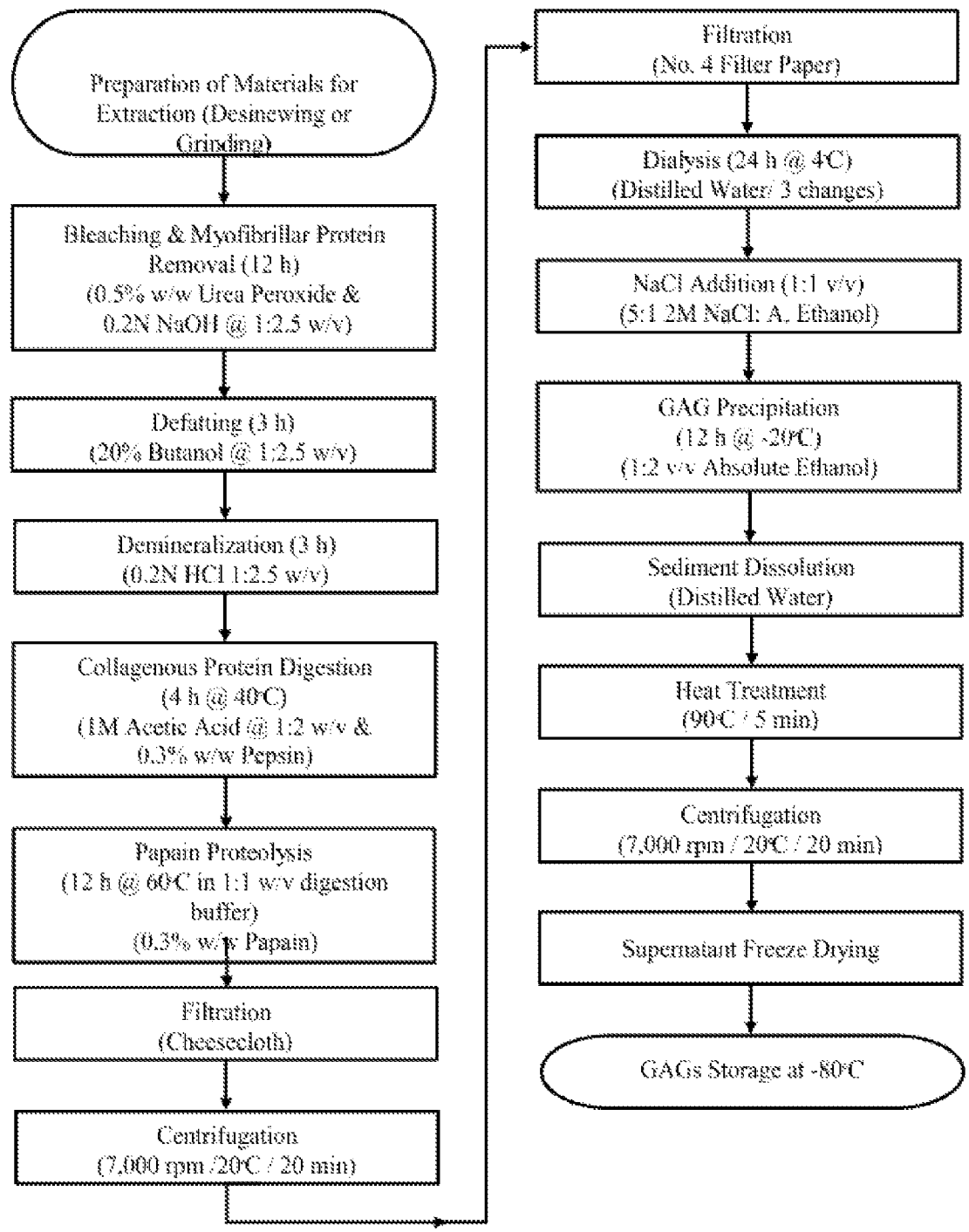
FIG. 1 depicts a process diagram of GAG extraction from alligator ACS, AFT and ABS.

A completely randomized block design (CRBD), with three GAG extractions (repetitions) as the blocking units, was used to test equality of means among treatments. The null ($H_o$: μ 1=μ2=μ3=μ4) and alternate ($H_a$: some μi is different) hypotheses were stated and all experiments and analyses were conducted in triplicates. Analyses of variance (ANOVA) using Proc GLM were conducted along with post-ANOVA Tukey pairwise tests using the Statistical Analysis System (SAS®) version 9.4. Results were reported as mean±standard deviation (SD), and differences were considered significant at $p \leq 0.05$.

Gene expression analyses were carried out in triplicate, and statistical analysis was performed using the SABiosciences PCR Array Data Analysis Web-based software, which calculated fold-regulation p-values using a Student's t-test on the fold-change values for each gene in the treatment group compared to the control group ($p \leq 0.05$). ANOVA and post-ANOVA Tukey pairwise tests using the Statistical Analysis System (SAS®) version 9.4 were conducted to evaluate RNA purity and PCR control gene expression. Results are presented as mean±standard error (SE) ($p \leq 0.05$).

Materials

Butyl alcohol (Cat. No. W217820), 2-mercaptoethanol (Cat. No. M-7154), absolute ethanol for molecular biology (Cat. No. E7023), porcine pepsin (Cat. No. P7125), L-cysteine (Cat. No. W326305), ethylenediaminetetraacetic acid (EDTA) (Cat. No. E9884), sodium chloride (Cat. No. 793566), crystalline carbazole (Cat. No. C5132), sodium tetraborate decahydrate (Cat. No. B9876), HAase type 1 from bovine testes (607 U/mg) (Cat. No. H3506), ChrAse ABC from *Proteus vulgaris* (Cat. No. C3667), CS-A from bovine trachea (Cat. No. C9819), Stains-All 95% (Cat. No. E9379), gel loading buffer (Cat. No. G2526), single use micro DispoDialyzers™ (50 kDa molecular weight cut-off (MWCO)) (Cat. No. D9187) and dialysis cellulose tubing (14 kDa MWCO) (Cat. No. D9402) were all purchased from Sigma Aldrich (St. Louis, Mo.).

Absolute ethanol 200 proof (Cat. No. 111000200) was purchased from VWR (Radnor, Pa.).

Sodium hydroxide (Cat. No. S318-3), acetic acid (Cat. No. UN2789), urea peroxide (Cat. No. ACS241020010), EMD Millipore ACS grade sulfuric acid (Cat. No. MSX1244PC5), hydrochloric acid (HCl) ACS grade (Cat. No. S25838), monobasic anhydrous sodium acetate (Cat. No. BP3331), Invitrogen™ Novex™ sharp pre-stained protein standard (Cat. No. LC5800) and HA standard from *Streptococcus* sp. (94%) (Cat. No. AC251770010) were obtained from Fisher Scientific (Pittsburgh, Pa.).

Papain (Cat. No. 102566) was acquired from MP Biomedicals (Santa Ana, Calif.).

UltraPure™ agarose (Cat. No. 16500500), and tris borate-EDTA (TBE) buffer (Cat. No. 15581044) were obtained from Thermo Fisher Scientific (Waltham, Mass.).

Select-HA™ low polydispersity HA standards HiLadder (1648, 1138, 940, 667, 509 kDa) and LoLadder (509, 310, 213, 111, 30.2) (Cat. No. HYA-HILAD-20 and HYA-LO-LAD-20) were purchased from Hyalose (Oklahoma City, Okla.).

Bovine serum albumin (BSA) (Cat. No. SC-2323) was purchased from Santa Cruz Biotechnologies Inc. Dallas, Tex.).

Sodium phosphate (Cat. No. 0571), sucrose (Cat. No. 0335), and ultrapure grade Tris-HCl (Cat. No. 0234) were purchased from Amresco (Solon, Ohio).

For the CF ex-vivo mice study, retinoic acid (Cat. No. R2625), insulin (Cat. No. 91077c), transferrin (Cat. No. T8158), cholera toxin (Cat. No. C8052), bovine pituitary extract (Cat. No. P1476), pronase from *Streptomyces griseus* (Cat. No. 10165921001) and DNase 1 from bovine pancreas (Cat. No. DN25) were purchased from Sigma Aldrich (St. Louis, Mo.).

Corning™ Nu-Serum growth medium supplement (Cat. No. CB-51000), Y-27632 ROCK inhibitor (Cat. No. BDB562822), rat tail collagen I (Cat. No. CB-354249), Corning™ fetal bovine serum (FBS) (Cat. No. 11648647), methyl sulfoxide (>99.8%) (Cat. No. AC327182500), phosphate buffered saline solution (pH 7.4) (Cat. No. 10010031), recombinant mouse epidermal growth factor (Cat. No. PMG8041), Dulbecco's Modified Eagle Medium (DMEM)/Ham's F-12 (1:1) (HEPES) (Cat. No. 11330-032), Gibco™ penicillin-streptomycin (10,000 U/ml; 10,000 mg/ml) (Cat. No. 15-140-122), Corning™ Primaria™ tissue culture dishes (Cat. No. 08-772-4A), Corning™ Costar™ Tran-swell™ clear polyester membrane inserts for 12-well plates (Cat. No. 07-200-161) and Falcon™ 6-well tissue culture plates (Cat. No. 0877233) were obtained from Fisher Scientific (Pittsburgh, Pa.).

Extraction of GAGs from Alligator Carcasses, Feet and Backstraps

Farmed alligator feet (AFT) (2 anterior & 2 posterior) and alligator backstraps (ABS) were collected from Vermilion Gator Farm Inc. in Abbeville, La. Waste alligator carcasses (ACS) were provided by Jacques' Croc's and Farm Pride (Scott, La.). All animals were between 12 and 18 months old at the time of slaughter. Samples were kept at −20° C. until used for GAG extraction.

A Baader® 693 bone separator (Indianola, Miss.) was used to process ACS and separate bones from meat. Three passes through a perforated stainless steel drum (Ø=3 mm) were performed at increasing belt pressures (20, 30 and 40 bar). Only bones including connective tissue were used for GAG extraction from ACS. AFT and ABS were ground in a Hobart HCM450 grinder-mixer (Troy, Ohio) prior to GAG extraction. An embodiment of the extraction process is illustrated in FIG. 1. To remove non-collagens proteins and to bleach skin pigments, the ACS, AFT or ABS samples were mixed with 0.2 N NaOH at a sample:solution ratio of 1:2.5 (w/v). In addition to the NaOH, the solution also contained 0.5% (w/w) urea peroxide. The mixture was stirred intermittently for 12 h with a solution change after 6 h. The deproteinized samples were defatted with 20% butyl alcohol (1:2.5 w/v) for 3 h. To remove inorganic compounds the samples were soaked in a 0.2 N HCl solution (1:2.5 w/v) for 3 h with manual stirring once every hour. Samples were filtered through cheese cloth and washed in running tap water after each step. For collagen proteolysis, the deproteinized, defatted and demineralized samples were finely ground and mixed with 1 M acetic acid (1:2 w/v) and pepsin (0.3% w/w). Pepsin proteolysis was conducted for 4 h at 40° C., followed by addition of papain (0.3% w/w) for 12 h at 60° C. Prior to use, the papain had been activated in 1:1 (w/v) digestion buffer (100 mM Na acetate, 5 mM L-cysteine, 5 mM EDTA). A double layer of cheesecloth was used to filter the resulting mixture, and the filtrate was collected, centrifuged (7,000 rpm/20 min/20° C.) and filtered again using filter paper (Whatman No. 4). Samples were dialyzed at 4° C. using a 14 kDa MWCO cellulose membrane against distilled water for 24 h, with solution changes every 8 h. The dialyzed samples were mixed (1:1 v/v) with a solution comprising 2 M NaCl aqueous solution:absolute ethanol (5:1). Absolute ethanol was added (1:2 v/v), and GAGs were precipitated for 12 h at −20° C. The pellet was dissolved in distilled water prior to a heat treatment (90° C./5 min) to inactivate enzymes and to disinfect the samples. Finally, samples were centrifuged, the pellets were discarded, and the supernatants were freeze-dried in a VirTis Genesis 35XL pilot lyophilizer (Stone Ridge, N.Y.) for 24 hours. Dried samples (<5.0% moisture content) were stored at −80° C. until analyzed.

Extraction of GAGs from Alligator Eyeballs

Figure 2:
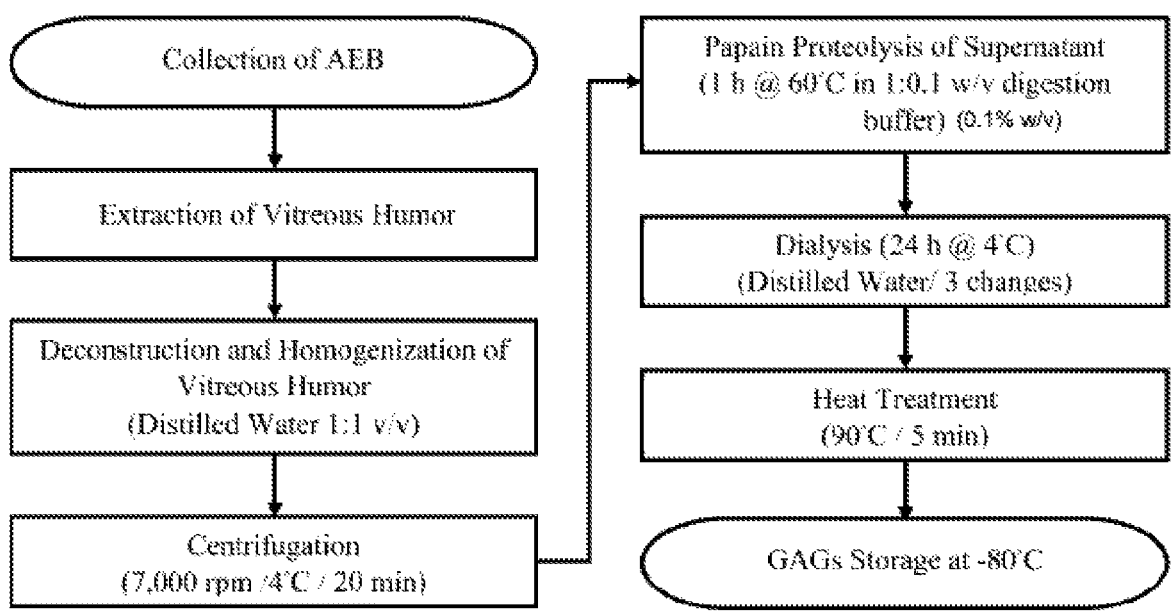
FIG. 2 depicts a process diagram of GAG extraction from AEB

Farmed alligator eyeballs (AEB) were manually collected from heads at Vermilion Gator Farm Inc. in Abbeville, La. AEB were cut vertically in half using a sharp scalpel to extract the vitreous humor (FIG. 2). Subsequently, the vitreous humor was dissolved in distilled water (1:1 v/v) and homogenized. Subsequently, the mixture was clarified by centrifugation at 7,000 rpm (20 min/4° C.). Two clear phases were obtained: dark sediment of impurities and a majority of vitreous humor supernatant. The supernatant was collected and its protein was hydrolyzed using papain in digestion buffer as described above. Samples were dialyzed at 4° C.

using a 14 kDa MWCO membrane against distilled water for 24 h, with solution changes every 8 h. The samples were heat-treated (90° C./5 min) and stored at −80° C. until used.

Determination of Sulfated GAGs, HA and Total GAGs Content

The sulfated GAG content was determined using a Chondrex Inc. (Redmond, Wash.) dimethylmethylene blue (DMB) assay (Cat. No. 6022), following the method of Garnjanagoonchorn and others. Calibration curves were developed using a chondroitin-6-sulfate standard. Samples were solubilized and diluted with PBS to fit the standard range. One hundred microliters of standards, samples and sample blanks were added in triplicates to a 96-well plate. Subsequently, a 1,9-DMB solution (100 µl) was added into the standard and sample wells, while PBS (100 µl) was added into the sample blanks. The plate absorbance was read at 525 nm within 5 min of DMB addition in a Bio-Rad Benchmark Plus Microplate Spectrophotometer (Philadelphia, Pa.). The sulfated GAG content was calculated by regression analysis. HA content was measured using an Echelon® competitive ELISA kit (50-1600 ng/ml) (K-1200, Echelon Biosciences Inc., Salt Lake City, Utah), which detected molecules as small as 6.4 kDa. The manufacturer's protocols were followed. Briefly, 100 µl of HA standards and diluted samples were added into a 96-well incubation plate followed by 50 µl of detection solution, prior to incubation for 1 h at 37° C. Following the incubation, samples (100 µl) were transferred into a detection plate for competitive binding at 4.0 for 30 min. The plate was then washed three times with 200 µl PBS-Tween (PBST), before addition of an enzyme-linked antibody and substrate solution. Colorimetric detection at 405 nm was used to detect the enzyme-substrate system, comprising an alkaline phosphatase/pNPP phosphatase substrate. The strength of the colorimetric signal inversely correlated with the HA content of the sample. A standard curve was prepared with known amounts of HA. The total GAG content of the extracted materials was calculated by addition the results of the two analyses described above, and further confirmed using a carbazole reaction to measure uronic acid after hydrolysis of GAGs with sulfuric acid. The absorbance of samples was measured at 550 nm, and GAG content was calculated by regression analysis using a HA-sodium salt standard curve.

GAG Size Analysis

The molecular weight of GAGs was evaluated by agarose gel electrophoresis. Agarose gels (0.75% w/v) were first prepared. The agarose solution was cooled under running tap water for 3 min, and then mixed with 4 ml of 10×TBE buffer to make a final gel volume of 40 ml. Gels of 10×6.2 cm were cast in a casting accessory using an 8-tooth, well-forming comb. Before electrophoresis, gels were allowed to set for at least 1 h. To load samples, the comb was removed and the gel plate was transferred to a Bio-Rad (Hercules, Calif.) Mini-Sub® Cell GT system, which was filled with 290 ml of pre-chilled 1×TBE buffer. Cells were loaded with samples (3 µg GAGs/well in ultrapure water) and GAG standards (HA & CS), which were mixed with 4 µl of 2 M sucrose loading buffer and sample volume made up to 24 µl with ultrapure water. SelectHA™ HiLadder (5 µl) and LoLadder (5 µl) standards were mixed with deionized water (10 µl) and loading buffer (4 µl) before being loaded into a well. Electrophoresis was carried out at room temperature at a constant voltage of 70 V for 2.5 h using a Bio-Rad Power-Pac™ power supply. The loading buffer tracking dye migrated about 80% of the gel's length during this time period. Immediately after the run the gel was placed in approximately 250 ml of a staining solution containing 0.005% Stains-All in 50% absolute ethanol (which had stored in the dark). The gel was stained overnight under light-protective cover at room temperature. For destaining, the gel was transferred to a 10% ethanol solution and stored in the dark for 8 h with at least one change of destaining solution. Final destaining of any residual background was accomplished by placing the gel on a light box for a few minutes.

Agarose gel electrophoresis was also performed on all samples after an alternative final dialysis step with single-use micro DispoDialyzers™. Briefly, dry GAG samples were dissolved in distilled, deionized water (100 µl) and placed in a floating sample chamber that separated the low molecular weight GAGs (<50 kDa) through a cellulose membrane and into the dialysis buffer (tap water). Samples were dialyzed with constant stirring for 48 h in 200 ml of buffer with changes every 2, 5, 15, 30 and 45 h. Samples were recovered into a micro centrifuge tube by centrifugation (1-2 s) at 1500 rpm. Electrophoresis was performed as described above.

Digestion of GAGs by Type-1 Hyaluronidase and Chondroitinase ABC

Digestion of ACS, AFT, ABS and AEB samples with a type 1 bovine testes HAase was conducted to demonstrate that the stained samples seen on the previously-described agarose gels were indeed GAGs. Phosphate Buffer (300 mM sodium phosphate, pH 5.35 at 37° C.) was used to prepare a 0.5 mg/ml GAG solution, which was completely dissolved and kept at 37° C. in a water bath. Immediately before use, a 24,000 U/ml HAase stock solution was prepared by dissolving the enzyme in enzyme diluent (20 mM sodium phosphate with 77 mM sodium chloride and 0.01% (w/v) BSA, pH 7.0 at 37° C.). Ultrapure water was used, and the pH was adjusted with 1 N NaOH or 1 N HCl. The stock solution was diluted with enzyme diluent to obtain additional working solutions of 12,000 U and 6,000 U. The final HAase assay concentrations (48, 24 and 12 U/µg sample) were obtained by mixing 0.5 ml of each GAG solution with 0.5 ml of enzyme solution (24,000, 12,000 or 6,000 U/ml). Incubation was conducted at 37° C. with continuous swirling for exactly 20 hours. HAase was heat-inactivated in a boiling water bath for 10 minutes before the mixture was centrifuged at 10,000 rpm for another 10 min. Supernatants were collected and stored at −80° C. until used.

An enzymatic assay using ChrAse ABC was conducted on ACS GAGs to further confirm the identity of the purple stains in agarose gels that had been stained with 0.005% Stains-All solution. A GAG solution in sample diluent (250 mM Tris-HCl and 300 mM sodium acetate with 0.05% (w/v) BSA, pH 8.0 at 37° C.) and a ChrAse ABC solution (0.4 U/ml) in 0.01% BSA were prepared. Working enzyme solutions (0.2 U/ml and 0.1 U/ml) were prepared from dilutions of stock solution. The final ChrAse assay concentrations (0.2, 0.1 and 0.05 U) were obtained by mixing equal parts of ACS sample solution and enzyme stock or working solutions. The mixtures were digested at 37° C. for 8 h with constant stirring, after which samples were boiled for 10 min, centrifuged at 10,000 rpm for 10 min, and stored at −80° C. until used. The results of the HAase and ChrAse ABC assays were evaluated by running all samples in 0.75% agarose gels and staining with 0.005% Stains-All as described previously.

Determination of Protein and Mineral Content

Protein content of the solubilized, purified GAG extracts was quantified by measuring absorbance at 562 nm using a Pierce™ Bicinchoninic Acid (BCA) Protein Assay (Philadelphia, Pa.). A series of dilutions of known concentrations of bovine serum albumin was used for standards, which were assayed alongside the GAG samples. GAG extract samples were prepared for mineral content determination by diluting 100 mg in deionized water (10 ml) and filtering through a 0.22 µm syringe filter. Concentration measurements of the filtered samples were carried out using inductively-coupled plasma atomic emission spectrometry (ICP-AES).

Structure Characterization by FT-IR Spectroscopy

A Bruker (Billerica, Mass.) Tensor 27 FT-IR spectrometer with a MIRacle™ single reflection diamond/ZnSe attenuated total reflectance cell (Pike Technologies, Madison, Wis.) was used to obtain FT-IR spectra of lyophilized ACS, AFT, ABS and AEB GAGs. Commercial HA and chondroitin-4-sulfate powders were analyzed and used as standards. The spectrum of each compacted dry sample was obtained over 50 scans in the range 650-4000 cm$^{-1}$, against a background spectrum recorded for the clean empty cell at room temperature. Spectral data analysis was conducted using OPUS data collection software version 7.2 (Bruker, Ettlinger, Germany). Atmospheric and baseline corrections were applied to the data, which were presented as wavenumber (cm$^{-1}$) versus normalized absorbance (min=0.0 and max=2.0).

Cystic Fibrosis Ex-Vivo Scnn1b-Tg Mice Pilot Studies

Transgenic Mice Generation and PCR Genotyping

All animal protocols were approved by the Louisiana State University's Institutional Animal Care and Use Committee. The transgenic mice used for this experiment were Scnn1b-Tg, a well-established murine model of CF and COPD. This C57BL/6N congenic mouse line over-expresses the β-subunit of the ENaC channel, which leads to ASL depletion and CF-like mucus obstruction. Moreover, Scnn1b-Tg mice recapitulate many key features of CF including high MIP-2, TNF-α, high TGAse activity, and neutrophilia. Genomic DNA extraction from mouse tail tissue was performed. Transgene-positive animals were identified by polymerase chain reaction (PCR).

All the Scnn1b-Tg mice used in the study were maintained in hot-washed, individually ventilated cages on a 12-hour dark/light cycle and were fed regular diet and water ad libitum. Mice were euthanized after establishment of chronic pulmonary disease, on post-natal day 38.

Trachea Harvesting

Mice (4 females) were euthanized by 2,2,2-tribromoethanol injection (300 µl/mouse) before being laid down (abdomen up) and disinfected (abdomen, thorax and neck) with 70% ethanol. Using clean surgical instruments, a horizontal cut from abdomen to neck skin was performed to expose the thoracic and neck regions prior to exsanguination via dissection of the abdominal aorta and puncturing of the diaphragm. Trachea were exposed by removal of surrounding tissue, and were removed by dissecting just below the vocal cords and at the carina bifurcation. All trachea were placed into a 50 ml conical tube containing 10 ml of cold Ham's F12 media containing antibiotics. In a sterile laminar flow hood, the trachea and Ham's F12 media containing antibiotics were cut open lengthwise to expose the lumen. Finally, trachea were placed in a 50 ml conical tube containing 10 ml of a solution prepared by mixing 9 ml of cold Ham's F12 with antibiotics and 1 ml of a filter-sterilized 1% pronase stock solution. The tube was incubated on a rocker overnight at 4° C. Subsequently, MTEC isolation and primary cell cultures were conducted.

MTEC Isolation.

After overnight incubation, 10 ml of Ham's F12 media containing 20% FBS and antibiotics were added to the tube, which was then rocked 12 times and then left to stand 30 min on ice. Tracheas were then transferred to a new conical tube containing 10 ml of Ham's F12 media with 20% FBS and antibiotics using a Pasteur pipette and rocked 12 times. This step was repeated two more times, and finally the remaining tissue was discarded. The pronase solution along with the three supernatants were pooled (50 ml total) and kept on ice until the mixture was centrifuged at 500×g for 5 min at 4° C. The supernatant was discarded and the pellet gently re-suspended and incubated 5 min on ice in 1 ml of a filter-sterilized DNase solution (0.5 mg/ml) prepared by dissolving 1.0 mg of DNase in 1.8 ml of Ham's F12 media containing antibiotics and 200 µl BSA stock solution (10 mg/ml). After incubation, the suspension was centrifuged (500×g for 5 min at 4° C.) to discard the supernatant, and the pellet was gently re-suspend in 5 ml of filter-sterilized MTEC basic media containing 10% FBS (Table 1). To remove fibroblasts, the suspension was plated on a Primaria™ tissue culture dish and incubated at 37° C. in a 5% $CO_2$ atmosphere for 4.5 hours. Following incubation, the cell suspension was collected and the plate was rinsed twice with 4 ml MTEC basic media containing 10% FBS. The cell suspension and washes were pooled together in a 50 ml conical tube and centrifuged (500×g for 5 min at 4° C.). The supernatant was discarded, and the pellet was re-suspended in 4.4 ml of filter-sterilized MTEC media containing Y27632 ROCK inhibitor (10 µM) (MTEC+Y27632). Cells were counted (10 µl cell suspension+10 µl trypan blue) in a Bio-Rad TC20™ automated cell counter (Bio-Rad Laboratories, Hercules, Calif.).

TABLE 1

MTEC Basic Media (10% PBS) Formulation

| Reagent | Final Concentration |
|---|---|
| DMEM/Ham's F-12 (HEPES) (1:1) | — |
| Penicillin-Streptomycin | 0.25 µg/ml |
| HEPES | 15 mM |
| Sodium Bicarbonate | 3.6 mM |
| L-Glutamine | 4 mM |
| Fetal Bovine Serum | 10% |

MTEC Submerged Culture

Six Transwell™ polyester membrane inserts were coated with 50 µg type I collagen dissolved in 165 µl of a solution prepared by mixing 0.02 N sterile acetic acid and collagen stock (8.31 µg/ul). The inserts were air-dried in a hood overnight, and were then exposed to ultraviolet light for 30 min before being seeded with 300 µl of the previously prepared cell suspension ($9.5 \times 10^4$ cells/insert). MTEC+Y27632 media (1 ml) (Table 2) was fed basally and cells were incubated overnight at 37° C. in a 5% $CO_2$ atmosphere. On the first day post-seeding, the apical media and non-adherent cells were aspirated. The inserts were then washed twice with 1 ml PBS and transferred to a 6-well plate with previously autoclaved polytetrafluoroethylene (PTFE) rings. The cultures were fed every other day with 2.5 ml MTEC+Y27632 media basally and 50 apically until confluent (7 days). The apical surface was washed gently once a week by adding 0.5 ml of PBS to the insert and carefully aspirating with a Pasteur pipette.

TABLE 2

MTEC + Y27632 Media Formulation

| Reagent | Final Concentration |
| --- | --- |
| DMEM/Ham's F-12 (HEPES) (1:1) | — |
| Penicillin-Streptomycin | 100 U/ml: 100 mg/ml |
| Insulin | 10 µg/ml |
| Epidermal Growth Factor | 25 ng/ml |
| Transferrin | 5 µg/ml |
| Bovine Pituitary Extract | 30 µg/ml |
| Retinoic Acid | $5 \times 10^{-8}$ M |
| Fetal Bovine Serum | 5% |
| Cholera Toxin | 0.1 µg/ml |
| Y-27632 ROCK inhibitor | 10 µM |

MTEC Differentiation in Air-Liquid Interface Culture

Once confluent, cell cultures were changed to an air-liquid-interface (ALI) in a fresh 6-well tissue culture plate for differentiation. The cells were fed basally with 2.5 ml of MTEC media containing Nu-Serum growth medium supplement (MTEC+NuSerum) every other day during 21 days (Table 3). Fresh retinoic acid ($5 \times 10^{-8}$) was added to supplement the MTEC+NuSerum media every other day during the last 14 days of ALI culture. The apical surface was washed gently once a week by adding 0.5 ml of PBS to the insert and carefully aspirating with a Pasteur pipette.

TABLE 3

MTEC + NuSerum Media Formulation

| Reagent | Final Concentration |
| --- | --- |
| DMEM/Ham's F-12 (HEPES) (1:1) | — |
| Penicillin-Streptomycin | 100 U/ml: 100 mg/ml |
| Retinoic Acid | $5 \times 10^{-8}$ M |
| Nu-Serum | 2% |

MTEC Treatment with AEB GAGS

Once cells had differentiated (day 21 of ALI culture), the MTEC cultures were treated apically with 350 µl of a solution containing 1.43 mg AEB GAGs/ml in 0.9% saline (0.5 mg AEB GAGs/insert). MTEC cultures that had been treated only with saline (350 µl) were used as controls. The treatment solution was sterilized by autoclaving at 121° C. for 5 min. Cultures were maintained at 37° C. in a 5% $CO_2$ atmosphere. The treatment was terminated by aspiration of the supernatant after 24 h, and the supernatants were stored at −80° C. for further analysis.

Cell Lysis and RNA Purification

RNA was extracted from MTEC cultures using the RNeasy® Plus Mini Kit (Cat. No. 14134) from Qiagen (Valencia, Calif.) following the manufacturer's instructions in an Air Clean® 600 PCR Workstation (BioExpress, Kaysville, Utah). Appropriate RNA handling techniques were applied to avoid contamination. Briefly, cells were disrupted and lysates homogenized using QTAshredder spin columns (Qiagen Cat. No. 79654) placed in 2 ml micro-centrifuge tubes, which were centrifuged for 2 min at maximum speed in a Thermo Scientific Sorvall™ ST 16R Centrifuge (Kalkberg, Germany). The homogenized lysates were transferred to genomic DNA (gDNA) eliminator spin columns in 2 ml collection tubes, which were centrifuged for 30 s at 8,000×g. The flow-through was saved, and one volume of 70% ethanol was added and mixed gently by pipetting. The samples were then transferred to an RNeasy spin column in a collection tube and centrifuged for 15 s at 8,000×g to discard the flow-through and elute the RNA from the column by centrifugation with 40 µl of RNase-free water. RNA concentration (260 nm) and purity ($A_{260}/A_{280}$) in the eluate (1 µl) were measured by UV spectrophotometry with a NanoDrop 2000 from Thermo Scientific (Wilmington, Del.), and RNase-free water as a blank. RNA samples (2 ng/µl) were submitted to the LSU School of Veterinary Medicine GeneLab for RNA integrity number calculation (RIN), and 18S and 28S fragment visualization using a Fragment Analyzer™ (Advanced Analytical Technologies Inc., Ames, Iowa).

cDNA Generation and PCR Microarray

Purified RNA (0.33 µg) was used to generate cDNA using the $RT^2$ First Strad Kit from Qiagen, with a genomic DNA elimination step and reverse transcription at 42° C. for 15 min. SYBR® Green based real-time PCR was performed using a murine CF $RT^2$ Profiler PCR Array, which profiles the expression of 84 key CF genes involved in neutrophil chemotaxis, inflammation, immune response and oxidative stress, among others (Table 4) in a 96-well plate format. The arrays included genomic DNA (GDC), reverse-transcription (RTC), and positive PCR controls (PPC). Manufacturer protocols were followed. PCR was conducted in a CFX96 Real-Time System equipped with CFX Manager™ Software and automatic threshold cycle ($C_T$) calculation from Bio-Rad Laboratories (Hercules, Calif.). The real-time cycler was first programed to cycle for 10 min at 95° C. to activate the HotStart DNA Taq Polymerase. This cycle was followed by 40 cycles of annealing for 15 s at 95° C. and elongation for 1 min at 60° C. with fluorescence data collection. The temperature ramp rate was adjusted to 1° C./s. Finally, a melting curve (65° C. to 95° C. at 0.5° C./s for 5 s) analysis was conducted to verify PCR specificity, as evidenced by a single peak for each reaction at temperatures greater than 80° C. CT values for all wells were processed with the SABiosciences PCR Array Data Analysis Web-based software. The software calculated $\Delta C_T$ ($C_T$ Gene of Interest–$C_T$ Housekeeping Gene) based on the B2m housekeeping gene and then calculated the normalized gene expression values using the formula $2^{\wedge}{-\Delta C_T}$. The fold-change values were then converted to fold-regulation. The software also performed a hierarchical cluster analysis of the dataset to generate a gene expression heat map (fold-regulation >1.5 and p≤0.05), with dendrograms indicating co-regulated genes across arrays. A heat map for all the 84 genes analyzed was also generated.

TABLE 4

Murine CF RT2 Profiler PCR Array Gene List*

| Gene ID | Official Name |
| --- | --- |
| CF Modifier Genes | |
| Adipor2 | adiponectin receptor 2 |
| Gstm2 | glutathione S-transferase, mu 2 |
| Ifrd1 | interferon-related developmental regulator 1 |
| Msra | methionine sulfoxide reductase A |

TABLE 4-continued

Murine CF RT2 Profiler PCR Array Gene List*

| Gene ID | Official Name |
|---|---|
| Nos3 (eNOS) | nitric oxide synthase 3, endothelial cell |
| Tcf7l2 | transcription factor 7 like 2, T cell specific |

CFTR Interactors

| | |
|---|---|
| Ahsa1 | AHA1, activator of heat shock protein ATPase 1 |
| Canx | Calnexin |
| Cftr | cystic fibrosis transmembrane conductance, regulator |
| Dnaja1 | DnaJ heat shock protein family (Hsp40) member A1 |
| Dnajc5 | DnaJ heat shock protein family (Hsp40) member C5 |
| Ezr | ezrin |
| Gopc | golgi associated PDZ and coded-coil motif containing |
| Hsp90aa1 (Hsapca) | heat shock protein 90, alpha (cytosolic), class A member 1 |
| Hspa4 (Hsp70) | heat shock protein 4 |
| Nme1 (NM23A) | NME/NM23 nucleoside diphosphate kinase 1 |
| Pdzk1 | PDZ domain containing 1 |
| Ppp2r4 | protein phosphatase 2 regulatory subunit 4 |
| Prkaa1 (Ampk) | protein kinase, AMP-activated, alpha 1 catalytic subunit |
| Prkaa2 | protein kinase, AMP-activated, alpha 2 catalytic subunit |
| Slc26a3 | solute carrier family 26, member 3 |

CFTR Interactors

| | |
|---|---|
| Slc9a3r1 | solute carrier family 9 (sodium(hydrogen exchanger), member 3 regulator 1 |
| Slc9a3r2 | solute carrier family 9 (sodium/hydrogen exchanger), member 3 regulator 2 |
| Snap23 | synaptosomal-associated protein 23 |
| Stx1a | syntaxin 1A |
| Stx8 | syntaxin 8 |
| Tjp1 | tight junction protein 1 |
| Vcp | valosin containing protein |

Neutrophil Chemotaxis

| | |
|---|---|
| Cel12 (MCP-5, Scya12) | chemokine (C-C motif) ligand 12 |
| Cxcr2 (IL-8rβ) | chemokine (C-X-C motif) receptor 2 |
| Edn1 | endothelin 1 |
| Ednra | endothelin receptor type A |
| IL-1β | interleukin 1 beta |
| Itgb2 | integrin beta 2 |

Inflammatory Response

| | |
|---|---|
| Ace | angiotensin I converting enzyme |
| Adrb2 | adrenergic receptor, beta 2 |
| Alox12b | arachidonate 12-lipoxygenase, 12R type |
| Cxcl1 (Gro1) | chemokine (C-X-C motif) ligand 1 |
| Cxcl3 | chemokine (C-X-C motif) ligand 3 |
| Defb1 | defensin beta 1 |
| IL-10 | interleukin 10 |
| IL-6 | interleukin 6 |
| Mbl2 | mannose-binding lectin (protein C) 2 |
| Pla2g5 | phospholipase A2, group V |
| Ptgs2 (COX) | prostaglandin-endoperoxide synihase 2 |
| S100a8 | S100 calcium binding protein A8 |
| S100a9 | S100 calcium binding protein A9 |
| Serpinale | serine (or cysteine) peptidase inhibitor |
| Tgfb1 | transforming growth factor, beta 1 |
| Tlr2 | tool-like receptor 2 |
| Tlr4 | tool-like receptor 4 |
| Tlr5 | tool-like receptor 5 |
| Tnf | tumor necrosis factor |
| Tnfrsf11a (Rank) | tumor necrosis factor receptor superfamily, member 11a, NF-κβ activator |
| Tnfrsf1a (Tnfr1) | tumor necrosis factor receptor superfamily, member 1a |

Immune Response

| | |
|---|---|
| Clu | clusterin |
| Icam1 | intercellular adhesion molecule 1 |
| Lcn2 (NGAL) | lipocalin 2 |
| Mapk1 (Erk2) | mitogen-activated protein kinase 1 |
| NF-Kβ1 | nuclear factor of kappa light polypeptide gene enhancer in B cells 1, p105 |
| NF-Kβia (IKβα, Mad3) | nuclear factor of kappa light polypeptide gene enhancer in B cells inhibitor, alpha |
| Prkce | protein kinase C, epsilon |
| Tnfsf10 (Trail) | tumor necrosis factor (ligand) superfamily, member 10 |

TABLE 4-continued

Murine CF RT2 Profiler PCR Array Gene List*

| Gene ID | Official Name |
|---|---|
| Fas (Tnfrsf6) | Fas (TNF receptor superfamily member 6) |
| IL-7r | interleukin 7 receptor |
| | Unfolded Protein Response |
| Calr | Calreticulin |
| Hspa1a (hsp70A1) | heat shock protein 1A |
| Hspa8 | heat shock protein 8 |
| Hsph1 (hsp105) | heat shock 105 kDa/110 kDa protein 1 |
| | Ion Binding & Transport |
| Adk | adenosine kinase |
| Kcne1 | potassium voltage-gated channel, Isk-related subfamily, member 1 |
| Nr4a2 (Nurr1) | nuclear receptor subfamily 4, group A, member 2 |
| Scnn1b | sodium channel, nonvoltage-gated 1 beta |
| Scnn1g | sodium channel, nonvoltage-gated 1 gamma |
| | Oxidative Stress |
| Dusp1 (Ptpn16) | dual specificity phosphatase 1 |
| Gclc | glutamate-cysteine ligase, catalytic subunit |
| Sftpb | surfactant associated protein B |
| | Other CF Genes |
| Epsti1 | epithelial stromal interaction 1 (breast) |
| Igfbp5 | insulin-like growth factor binding protein 5 |
| Itga2 | integrin alpha 2 |
| Kit (CD117) | kit oncogene |
| Met | met proto-oncogene |
| Prtn3 | proteinase 3 |
| Slpi | secretory leukocyte peptidase inhibitor |

*Genes might be relevant in more than one CF pathway.

Transglutaminase Activity Assay

Extracellular TGAse activity in MTEC was measured spectrophotometrically (450 nm) using a TGAse Assay Kit from Sigma-Aldrich (Cat. No. CS1070). Manufacturer's protocols were followed. The assay is based on the TGAse catalysis of a covalent bond between a free amine group of poly-L-lysine, which is covalently bonded to a 96-well plate surface, and the γ-carboxamide group of a biotin substrate buffer. The amount of immobilized biotin was proportional to the amount of active TGAse.

Results and Discussion

Yields of Sulfated GAG, HA and Total GAG from Alligator by-Products

Waste byproducts of farmed alligators 12 to 18-months old with approximate snout to tail length of 4 feet, had means as reported in Table 5. These values represent results from 80 ACS, 400 AFT, 100 ABS, and AEB from 200 alligator heads. Alligators from different farms or development stages may show differences in these measurements.

TABLE 5

Alligator By-product Processing Results

| | By-product | | | |
|---|---|---|---|---|
| | ACS (n = 80) | AFT (n = 100)* | ABS (n = 100) | AEB (n = 200) |
| Weight (g) | 942.00 ± 109.12 | 105.84 ± 6.93 | 68.44 ± 12.46 | 2.67 ± 0.19 |
| Meat Yield (% w/w) | 74.34 ± 2.72 | — | — | — |
| Bone Yield (% w/w) | 22.46 ± 3.88 | — | — | — |

TABLE 5-continued

Alligator By-product Processing Results

| | By-product | | | |
|---|---|---|---|---|
| | ACS (n = 80) | AFT (n = 100)* | ABS (n = 100) | AEB (n = 200) |
| Vitreous Humor Yield (% w/w) | — | — | — | 25.85 ± 2.24 |

Means ± SD are shown.

ACS = alligator carcasses, AFT - alligator feet, ABS = alligator backstraps, AEB = alligator eyeballs.

*Average weight of two anterior and two posterior feet is reported.

Purified GAGs from farmed alligator by-products were obtained by a series of optimized physical and chemical processes including removal of myofibrillar proteins and fat, enzymatic hydrolysis of collagenous protein and purification by dialysis, as well as NaCl-ethanol precipitation, heat treatment and lyophilization. The sulfated GAG yields (Table 6) as determined by the DMB assay were highest ($p \leq 0.05$) in ABS (0.22±0.01 mg/g wet ABS), followed by AFT, ACS and AEB. The calibration curve for this assay showed a linear relation between absorption at 525 nm for chondroitin sulfate-DMB complexes versus concentration of CS in the solution, with a correlation coefficient ($R2$) of 0.975.

TABLE 6

Composition of Alligator GAGs

| By-product | Sulfated GAGs (mg/g of wet by-product) | HA Content (mg/g of wet by-product) | Total GAGs (mg/g of wet by-product)† | Total GAGs (mg/g of wet by-product)†† |
|---|---|---|---|---|
| ACS | 0.00 ± 0.00$^{c*}$ | 0.60 ± 0.00$^d$ | 0.60 ± 0.00$^d$ | 0.63 ± 0.03$^c$ |
| AFT | 0.10 ± 0.01$^b$ | 4.62 ± 0.06$^b$ | 4.72 ± 0.05$^b$ | 4.98 ± 0.73$^b$ |
| ABS | 0.22 ± 0.01$^a$ | 15.31 ± 0.26$^a$ | 15.53 ± 0.27$^a$ | 16.66 ± 2.34$^a$ |
| AEB | 0.01 ± 0.01$^c$ | 0.78 ± 0.01$^c$ | 0.79 ± 0.01$^c$ | 0.83 ± 0.04$^c$ |

Means ± SD are shown.
ACS = alligator carcasses, AFT = alligator feet, ABS = alligator backstraps, AEB = alligator eyeballs.
*Means that do not share a letter within a column are significantly different ($p \leq 0.05$).
†Total GAGs (mg) = Sulfated GAGs (mg) + Hyaluronic Acid (mg)
††Total GAGs measured by the 96-well carbazole reaction.

Quantitation of HA concentrations by ELISA using a standard curve generated by non-linear regression analysis gave yields of 0.60±0.00, 4.62±0.06, 15.31±0.26 and 0.78±0.01 mg per gram of wet ACS, AFT, ABS and AEB, respectively (Table 6). The total concentration of GAGs (including sulfated GAGs) was calculated to be 0.60±0.00 (0.06% w/w), 4.72±0.05 (0.47% w/w), 15.53±0.27 (1.55% w/w) and 0.79±0.01 (0.08% w/w) mg/g of wet ACS, AFT, ABS and AEB, respectively. Non-sulfated HA accounted for 97.87-99.48% of the extracted GAGs. The highest yield per gram was obtained from ABS, followed by AFT, AEB and ACS. Based on the average by-product weight data reported in Table 5 and the average yields reported in Table 6 (average by-product weight×average total GAG yield), the estimated total GAG yields from one farmed alligator (~4 ft.) are highest in ABS (1.06 g/backstrap), while ACS (0.57 g/carcass) and AFT (0.50 g/4 feet) have similar contents, and AEB (0.004 g/two eyes) have the lowest yields. These results are equivalent to approximately 2.13 g total GAGs recovered per alligator. In 2014, a total of 341,887 farmed alligators were slaughtered in Louisiana, equivalent to a potential yield of about 0.73 metric tons of extractable GAGs, of which over 97% is HA.

A 96-well assay for uronic acid carbazole reaction has been reported for the determination of uronic acid complexes containing GAGs. In our samples, the carbazole assay further confirmed the presence of uronic-acid containing polysaccharides (Table 6). However, there was a slight (4.76-6.78%) overestimate of total GAG content as compared to the additive procedure (sulfated GAG concentration+HA concentration). The 96-well carbazole assay may overestimate GAGs in the presence of salts.

Several publications have reported yields from chicken combs ranging from 1 to 4 mg hexuronic acid/g wet tissue. Our higher yields per gram from AFT and ABS indicate that these by-products are promising when compared to this well-established source of HA. The novel process for extracting GAGs from alligator byproducts achieves high yields, showing that this is a good source for these compounds. The main by-product from alligator processing by weight is ACS. Its high availability, in addition to the potential added-value of desinewed meat, justify its use for GAG extraction despite its lower extraction yield as compared to ABS and AFT.

Even with a lower GAG content per alligator, AEB is a viable source of HA due to its highly pure abundance in the vitreous humor, which facilitates its extraction and purification, compared to ACS, AFT and ABS. Moreover, the AEB HA yield obtained in this study (0.78 mg/g eyes or ~3.02 mg/g vitreous humor) is much higher than the concentrations than has been reported from other sources. Our results are at least two times higher than have been reported from bovine vitreous humor (0.3 mg/g), swordfish vitreous humor (0.055 mg/g), shark vitreous humor (0.3 mg/g), and pig vitreous humor (0.04 mg/g). Our superior yields may be due both to differences between species and the extraction procedures we employed.

Agarose Gel Electrophoresis of Alligator GAGs

The molecular weight of GAGs is an important factor in its biological activity. To estimate the molecular weight of GAGs from ACS, AFT, ABS and AEB, agarose gel electrophoresis was performed, along with electrophoresis of GAG standards, on a 0.75% agarose gel stained with Stains-All. We observed primarily blue staining on all samples, indicating the presence of HA. The polydisperse distribution of molecular weight in HA from animal tissues was evident in the GAGs from ACS (~110-1600 kDa), AFT (~70-510 kDa), ABS (~15-1100 kDa) and AEB (~25-1600 kDa). CS was visualized on ACS (<70 kDa) as a purple-reddish smear. Sulfated fractions were not observed from AFT, ABS, and AEB, which might indicate that they migrated faster due to their lower molecular weight, and may have simply run ran off the gel.

Agarose gel electrophoresis of the GAG samples was also conducted after dialysis in a small volume (100 µL) sample chamber with a cellulose membrane against water. Dialysis for 48 hours essentially removed HA below ~28 kDa, and LMW sulfated GAGs from all samples. When desired, further purification and specific molecular weight separations can be conducted on samples prepared in accordance with the present invention, using methods known in the art such as size exclusion chromatography.

Enzymatic Assays

Alligator GAG samples were digested with HAase from bovine testes as negative controls to demonstrate that the stains seen were indeed from GAGs. Our observations showed that increasing the concentration of HAase resulted in greater depolymerization of the GAG samples, indicating the presence of HA and CS in the extracts. HAase randomly hydrolyzes 1,4-linkages between GlcNAc and GlcA in HA; as well as 1,4-linkages between GalNAc or sulfated GalNAc and GlcA in all types of CS, at an optimum pH of 4.5-6.0. HA degradation patterns were similar in all samples. Increased concentrations of HAase resulted in increased HA hydrolysis, seen as stains with lower molecular weight or lighter colored bands. ABS showed overall HA degradation above 700 kDa and below 33 kDa. However, there were also bands around 300-400 kDa in the 12 and 24 U/µg treatments (ABS lanes 3 and 4). This observation might be due to accumulated hydrolyzed HA chains of that particular molecular weight, or it might be due to transglycosylation. Transglycosylation activity of HAase in the presence of 6 to 12 monomer HA units has been previously reported to yield HA oligosaccharides at a pH-7 and salt content below 0.5 M.

ChrAse ABC was used to catalyze the degradation of polysaccharides containing 1,4 and 1,3 linkages. This effect was observed on both non-sulfated and sulfated GAGs in ACS. The GAGs hydrolyzed by ChrAse ABC include C4S, C6S, DS and HA. Even though HA is degraded at a lower rate, this effect was clearly seen in our assay. ChrAses A, C, AC and ABC act upon HA. However, ChrAse B is specific for cleavage of DS. Our results showed that the purple stains observed in the agarose gels corresponded to a type of CS. Dialysis or size exclusion chromatography might be a better option to preserve BMW and MMW HA during the elimination of LMW GAGs.

Protein and Mineral Content of Alligator by-Product GAGs

Extracts from ACS, AFT, ABS and AEB were analyzed for residual protein by the BCA assay at 562 nm. These by-products are high in muscle or collagen protein content. Sequential pepsin and papain digestions were conducted to yield clear solutions after 16 hours at 40° C. and 60° C., respectively. AEB extracts in particular had low protein content and high purity (~99%).

A significant problem in HA purification is the elimination of various proteins that can be allergenic. For injection purposes (e.g., dermal fillers), the protein concentration should be no more than ~5-10 μg of protein/mg HA; with somewhat higher tolerance for topical, perfusion or oral intake applications. The specifications of the European and British Pharmacopoeia allow 0.1-0.3% protein in HA. By contrast, in the United States commercially available HA has been reported to contain up to 4.7% protein. Against this background, AEB-derived HA is well-suited for uses where low protein levels are desirable, including for example osteoarthritis visco-supplements, ophthalmic viscoelastic adjuvants, aesthetic surgery adjuvants, eye drops, and topical preparations for wound and burn healing. At higher protein levels, HA from ACS (1.8%), AFT (2.65%) and ABS (3.68%) are suited for research applications and animal nutrition applications.

The final protein concentration resulting from the embodiment illustrated in FIG. 1 depends principally on these four steps: removal of muscle proteins with 0.2 N NaOH, pepsin and papain digestion, dialysis filtration, and NaCl-ethanol precipitation of GAGs. Protein levels could be further reduced through additional steps such as electrodeposition, filtration through activated charcoal, or size exclusion chromatography. As a general observation, further processing is likely to reduce the molecular weight of the extracted materials.

Mineral content in alligator by-product GAGs is predominantly sodium as measured by ICP-AES. The mineral levels were similar in ACS (13.92±0.20 mg/100 mg dry extract), AFT (10.64±0.20 mg/100 mg dry extract), and ABS (11.03±0.20 mg/100 mg dry extract), with sodium accounting for over 97% of the total in all three extracts. These results were not surprising, in view of the use of NaCl in performing the separations (See, e.g., FIG. 1). The 2 M concentration of NaCl used in this here was determined based on the efficiency of GAG recovery. Addition rates of 1 M, 1.5 M, 2 M and 4 M were evaluated. 2 M NaCl was more efficient than lower concentrations, but not significant improvement occurred at 4 M. NaCl (4 M) and CPC (10%) were also evaluated in combination, again with no significant increase in GAG recovery. Lower concentrations of NaCl could also lead to higher protein levels. AEB GAGs purified without NaCl precipitation had lower total mineral content (0.27±0.03 mg/100 mg dry extract); and $Na^+$ and $K^+$ were the predominant minerals then. Physiologically, HA typically occurs as a salt bound to cations, particularly $Na^+$ and $K^+$. Trace levels of other minerals were also detected in all samples, such as phosphorus, sulfur, and calcium. These other minerals presumably originate from sources such as bones, claws, and calcified scales.

FTIR Spectra of Alligator by-Product GAGs

The assignment of FTIR-ATR spectral bands for the various samples is given in Table 7. Commercial *Streptococcus* sp. HA and bovine trachea CS were used as standard references for data analysis and peak identification. All samples and standards displayed a strong absorption peak at 3258 $cm^{-1}$ to 3289 $cm^{-1}$, suggesting the stretching of —NH or —OH in the uronic acid —COOH group, as expected in GAGs. Lower absorption peaks near 3078 $cm^{-1}$ for samples and 3099 $cm^{-1}$ for standards are identified as the —NH and C═O combination in the amino sugar of GAGs, while minor peaks at 2890 and 2980 $cm^{-1}$ suggest —CH stretching. The FTIR spectra also revealed characteristic C═O vibrations associated with primary amides between 1627 $cm^{-1}$ and 1635 $cm^{-1}$. These peaks were not observed in the HA or CS standards. Secondary amide peaks were centered around 1600 $cm^{-1}$ for HA and CS standards, and at lower frequencies for alligator-derived samples (1538 $cm^{-1}$ to 1575 $cm^{-1}$). A peak in the range of 1222 $cm^{-1}$ to 1255 $cm^{-1}$ was observed in the CS standard, while alligator samples showed minor absorption in this region, consistent with the quantified sulfated GAGs content seen in Table 5. Absorption in the 1200 $cm^{-1}$ to 1250 $cm^{-1}$ range was not observed in the HA standard. Peaks in the range of 1000 $cm^{-1}$ and 1200 $cm^{-1}$ (C—OH, C—O and C—O—C) are characteristic of pyranose rings, which are the building blocks of GAGs. Below 1000 $cm^{-1}$, —OH deformations and C—O—C stretches were seen. Absorption at 855 $cm^{-1}$ indicated the presence of chondroitin-4-sulfate. In summary, fingerprint functional groups and structures associated with GAGs were identified in the 650-4000 $cm^{-1}$ FTIR spectra.

TABLE 7

Assignment of FTIR Bands for Standards and Alligator GAGs

| FTIR Bands | Funcational Groups | HA STD | CS STD | ACS | AFT | ABS | AEB |
|---|---|---|---|---|---|---|---|
| 1 | O—H or N—H stretching | 3271* | 3267 | 3258 | 3205 | 3272 | 3289 |
| 2 | N—H with C═O combination | 3095 | 3099 | 2070 | 3078 | 3979 | 3070 |
| 3 | C—H stretching | 2890 | 2891 | 2935 | 2959 | 2937 | 2980 |
| 4 | C═O carboxyl amide I | — | — | 1635 | 1631 | 1632 | 1627 |
| 5 | Amide II | 1602 | 1604 | 1546 | 1539 | 1538 | 1575 |
| 6 | N—H deformation | 1490 | 1442 | 1452 | 1452 | 1452 | 1453 |
| 7 | C—O with C═O combination | 1407 | 1409 | 1399 | 1399 | 1393 | 1404 |
| 8 | C—O—H deformation | 1375 | 1375 | — | — | — | — |
| 9 | S═O stretching | — | 1222 | 1255 | 1241 | 1245 | 1243 |
| 10 | C—O—H stretching, C—O and C—O—C | 1148 | 1155 | — | — | 1154 | 1121 |
| 11 |  | 1080 | 1080 | 1080 | 1080 | 1080 | 1081 |
| 12 |  | 1034 | 1023 | 1030 | 1029 | 1028 | 1042 |

TABLE 7-continued

Assignment of FTIR Bands for Standards and Alligator GAGs

| FTIR Bands | Funcational Groups | HA STD | CS STD | ACS | AFT | ABS | AEB |
|---|---|---|---|---|---|---|---|
| 13 | O—H deformation | 947 | 923 | 922 | 921 | 921 | 925 |
| 14 | C—O—C stretching | 895 | 887 | 882 | — | — | — |
| 15 | C4S Sulfate group | — | 855 | — | — | — | 855 |

*Peak absorbance wavenumbers (cm$^{-1}$) are shown.
HA STD = hyaluronic acid standard,
CS STD = chondroitin sulfate standard,
ACS = alligator carcasses,
AFT—alligator feet,
ABS—alligator backstraps,
AEB—alligator eyeballs.

AFT GAG samples were also submitted to Thermo Fisher Scientific for collection of FTIR spectra. The FTIR spectra were similar to those we had measured; however a more sharply defined fingerprint region was seen, perhaps from the use of newer and more sensitive equipment. Quenching of some fingerprint signals and the presence of amide peaks was attributed to the presence of residual collagen protein or peptides.

MTEC Gene Expression Analysis

To test the ability of AEB GAGS to regulate gene expression in CF-like MTEC ex-vivo cultures, we used the Scnn1b-Tg mice line that over-expresses the β-subunit of the ENaC channel and presents constitutive airway inflammation. Isolated Scnn1b-Tg MTECs yielded 3.49×10$^5$ live cells/trachea, which successfully proliferated in a submerged culture and differentiated at ALI into an intact monolayer with a cobblestone morphology. Murine epithelial primary cultures with these characteristics are used in the investigation of airway diseases and novel therapies. The ALI Transwell™ culture system allowed culturing the MTEC in conditions closer to the in vivo physiological conditions, which is an advantage as compared to conventional media submerged cultures.

RNA free of any major contaminants was successfully purified from MTEC control and treated cultures as indicated by the $A_{260}/A_{280}$ of 2.07±0.00 and 2.08±0.01, respectively (Table 8). These RNA quality parameters influence the efficiency of downstream reverse transcription procedures. High RNA Integrity Number (RIN) results (Table 8), as well as sharp peaks and bands for rRNA 5S, 18S and 28S fragments, were all indicators of RNA with very low degradation. RIN values above 5.5 are generally considered to yield high quality outcomes in rt-PCR. All samples passed quality control assays of the cDNA generation efficiency, genomic DNA contamination, and overall PCR performance. All the arrays presented similar (p≤0.05) reverse-transcription efficiencies (average RTC−average PPC≤5) which indicated that the data generated was suited for comparison (Table 8). Genomic DNA contamination did not contribute to the fluorescence signals captured during real-time PCR (GDC $C_T$≥35), and overall PCR reproducibility within and between arrays passed the manufacturer's approval parameters (Table 8).

TABLE 8

RNA Extraction kind PCR Control Results

| Reagent | Control (saline) | AEB GAGs Treated |
|---|---|---|
| RNA $A_{260}/A_{280}$ Ratio$^\ddagger$ | 2.07 ± 0.00*$^a$ | 2.08 ± 0.01$^a$ |
| RIN$^{\dagger\dagger}$ | 9.03 ± 0.06$^a$ | 8.93 ± 0.15$^a$ |

TABLE 8-continued

RNA Extraction kind PCR Control Results

| Reagent | Control (saline) | AEB GAGs Treated |
|---|---|---|
| $C_T$ GDC$^\xi$ | >35 | >35 |
| Reverse-Transcription Efficiency$^\varphi$ | 3.93 ± 0.06$^a$ | 4.11 ± 0.26$^a$ |
| PCR Array Reproducibility$^\Omega$ | | Pass |

*Means that do not share a letter within a row are significantly different.
$^\ddagger$A ratio of ~2 is generally accepted as "pure".
$^{\dagger\dagger}$Values range from 1 (totally degraded) to 10 (intact). RIN ≥ 7 is ideal.
$^\xi$GDC $C_T$ ≥ 35 is equal to "Pass".
$^\varphi$Average RTC $C_T$ - Average PPC $C_T$ ≤ 5 is equal to "Pass".
$^\Omega$If average PPC $C_T$ within an array is 20 ± 2 and average PPC $C_T$ of any two arrays is not more than 2 different from one another, then the sample receives a "Pass".

The gene expression analysis of PCR microarray data was conducted by setting a lower limit of detection ($C_T$<35), a ΔRn threshold above the automatically calculated background signal, a fold-regulation threshold (1.5), and normalization versus the B2m housekeeping gene—which was the most stably expressed across the evaluated samples (ΔAverage $C_T$<1). The genes that were not detected (9.52%) in at least one of the microarrays were not included in the analysis, namely Alox12b, Ccl12, Cxcr2, Il1b, Il10, Il6, S100a8, Serpina1e, Slc26a3. Seventy five (89.29%) of the genes analyzed were detected, and a heat map depicting their differential expression in MTEC cultures was analyzed (data not shown). Differential regulation of MTEC gene expression was evaluated after treatment with 0.5 mg AEB GAGs, as compared to controls. Without a fold-regulation threshold, 32.00% (24 genes) of the genes were significantly (p≤0.05) down-regulated and 4.00% (4 genes) up-regulated, while the rest of the genes were not significantly (p>0.05) down (42.67%) or up-regulated (21.33%). Overall shifts observed in the expression of 75 genes were indicative of the multiple signaling properties of HA in murine lungs through CD44, RHAMM, or TLR4. Another view of the potential effects of AEB GAGS in gene expression was from a volcano plot that included a 1.5 fold-regulation threshold (data not shown). With this additional criterion, expression of 34.67% of the genes remained essentially unchanged after AEB GAG treatment, and the percentage of significantly (p≤0.05) regulated genes also remained unchanged. Evaluation of the gene expression of wild-type MTEC cultures further confirmed and assisted in interpreting these results. We constructed a non-supervised hierarchical clustering heat map with dendrograms that graphically presented differences in the gene expression patterns between treated and control cell cultures. (data not shown) Gene clusters were based on similarities in their expression patterns, not any known functional similarities. In order of the magnitude of differential regulation changes, the significantly (p<0.05)

up-regulated (>1.5-fold) genes were Slpi, Cxcl1, and Lcn2 (Table 9). Following the same criteria, the significantly down-regulated genes were Kit, Hsph1, Itga2, Ace, Hsp90aa1, Tgfb1, Slc9a3r2, Ezr, Nfkb1, Slc9a3r1, Igfbp5, Tjp1, Adipor2, Prkaa1, Gopc, Prkce, Prkaa2, Ppp2r4, Hspa8, Sftpb, Nr4a2, Tlr4, Calr, and Tcf712. Other genes with non-significant (p>0.05) fold-regulation above 2-fold included S100a9 (2.18-fold; p-value=0.0778302), Ptgs2 (−3.78-fold; p-value=0.065190), Edn1 (−2.69-fold; p-value=0.123140), Dusp1 (−2.28-fold; p-value=0.062676), and Dnajc5 (−2.07-fold; p-value=0.056502).

Preliminary interpretations of these gene expression observations suggest that the HA from AEB induced anti-protease, anti-inflammatory, and ion-transport homeostatic effects on Scnn1b-Tg MTEC ex vivo cultures. We expect the HA from AEB will exert similar effects in vivo.

TABLE 9

Genes differentially expressed in HA treated vs untreated Scnn1b-Tg MTEC*

| Gene | Function | p-value | Fold-regulation |
|---|---|---|---|
| Up-Regulated | | | |
| Slpi | Protection of epithelial tissues from serine proteases | 0.0019 | 6.38 |
| Cxcl1 | Antimicrobial gene. Neutrophil chemoattractant | 0.0349 | 3.54 |
| Lcn2 | Antibacterial activity & oxidative stress protection | 0.0398 | 2.10 |
| Down-Regulated | | | |
| Kit | MAST cell adhesion to airway epithelia | 0.0036 | −3.88 |
| Hsph1 | Stress response | 0.0110 | −3.61 |
| Itga2 | Matrix metalloprotcinase-1 positive regulation | 0.0066 | −3.59 |
| Ace | Vasoconstrictor & pro-inflammatory mediator | 0.0011 | −3.35 |
| Hsp90aa1 | Endoplasmic reticulum stress response | 0.0027 | −3.35 |
| Tgfb1 | Fibrosis development & inflammatory response | 0.0094 | −3.33 |
| Slc9a3r2 | Trans-epithelial sodi urn/hydrogen absorption | 0.0105 | −3.25 |
| Ezr | Actin linking to the apical membrane & mucin secretion | 0.0305 | −3.23 |
| Nfkb1 | Positive regulator of inflammation | 0.0471 | −2.96 |
| Slc9a3r1 | Trans-epithelial sodium/hydrogen absorption | 0.0181 | −2.84 |
| Igfbp5 | Fibrosis development & ECM production | 0.0030 | −2.78 |
| Tjp1 | Regulation of cell polarity & tight junction regulation | 0.0148 | −2.69 |
| Adipor2 | Regulation of AMPK & PPAR-alpha metabolisms | 0.0031 | −2.56 |
| Prkaa1 | Metabolic regulation | 0.0498 | −2.42 |
| Gopc | Ion channel binding | 0.0277 | −2.41 |
| Prkce | Immune response modulation | 0.0023 | −2.35 |
| Prkaa2 | Metabolic regulation | 0.0188 | −2.28 |
| Ppp2r4 | Homeostatic balance of cell metabolism & signaling | 0.0359 | −2.18 |
| Hspa8 | Protein folding & cellular homeostasis | 0.0290 | −1.94 |
| Sftpb | Surfactant surface formation | 0.0273 | −1.94 |
| Nr4a2 | Modulation of inflammation & metabolism | 0.0458 | −1.92 |
| Tlr4 | Modulation of inflammation & immunity | 0.0114 | −1.85 |
| Calr | Ca2' binding & regulation of surface protein expression | 0.0333 | −1.79 |
| Tcf712 | Glucose metabolism & type 2 diabetes susceptibility | 0.0193 | −1.69 |

*Genes with significant (p ≤ 0.05) fold-regulation greater than 1.5-fold are presented.

The 6.38-fold upregulation of Slpi in AEB GAG treated cells compared to control was the highest and most significant (p=0.0019) differential change in gene regulation observed in this study (Table 9). The Slpi gene encodes a secretory leukocyte protease inhibitor, a serine anti-protease, that inhibits elastase, cathepsins, trypsin and chymotrypsin. Defects in airway mucosal defense, including disruption of the homeostatic protease/anti-protease balance, contribute to the pathogenesis of obstructive pulmonary disease in CF. Offsetting this imbalance is one of the therapeutic goals in CF management. Therapeutic approaches have included administration of Slpi and synthetic anti-proteases. An in-vivo study with sheep exposed to human elastase reported inhibition of elastase-related airway responses after treatment with aerosolized HA (150 and 300 kDa). It has also been reported that a single aerosol exposure (20 mg/mouse for 50 min) to streptococcal HA (100 kDa) reduced elastase-induced airspace enlargement in mice and prevented elastic fiber injury in-vitro. Overall, positive results regarding HA protection of airway fibers and regulation of acute lung injury have been reported. However there are no known reports of HA regulation of the Slpi gene in airway epithelial cells as observed in our results. HA has also been reported to immobilize and regulate other important components of the airway defense mechanism such as the serine protease tissue kallikrein and lactoperoxidase. Regulation of these enzymes is important for homeostasis at the apical mucosal surface. The down-regulation of Itga2 (−3.59-fold) shows the ability of AEB GAG treatment to mediate the protease/anti-protease imbalance characteristic of CF. Integrin α2β1 is a positive gene expression regulator of MMP-1, which is a serine collagenase known to be differentially upregulated during acute and chronic lung diseases as compared to healthy patients. Inhibition of expression or activation of MMPs could be used as therapy for CF and other chronic lung diseases.

Tgfb1 was down-regulated −3.33-fold in AEB GAG treated MTEC (Table 9). Tgfb1 encodes transforming growth factor-β, which promotes fibrosis through the deposition of ECM, promotes inflammation and modulates immune responses. Various mutations in the Tgfb1 gene have been associated with an accelerated decline in lung function of CF patients. Microarray cDNA analyses have shown that Tgfb1 upregulation alters the expression of multiple genes associated with acute lung injury in nickel-exposed mice. Fibrosis is generally viewed as failed wound healing, and can eventually lead to loss of lung function. The downregulation of Tgfb1 and Igfbp5 (−2.78-fold) (Table 9)

suggests it has potential for treating fibrosis. Studies have found increased expression of Igfbp5 in mice lung tissue after bleomycin-induced fibrosis, idiopathic pulmonary fibrosis in human lung sections, and severe emphysema of smokers in a chromosomal region strongly linked to FEV1. Our results support the conclusion that AEB GAGs can help protect Snn1b-Tg epithelial tissue from excessive degradation by proteases and from excessive remodeling during airway diseases. The roles of Slpi anti-protease activity and Tgfb1-related inflammation in wound healing and skin diseases such as psoriasis suggest that AEB GAGs can also be used in the treatment of inflammatory skin diseases.

The secretory leukocyte protease inhibitor encoded by Slpi has also been shown to inhibit inflammatory responses via different mechanisms, including competition with p65 for binding NF-κβ, which in turn prevents its activation and inhibition of neutrophil degranulation. Our study found anti-inflammatory effects in epithelial cells treated with AEB GAGs. Down-regulation of Ace (−3.59-fold), Nfkb1 (−2.96-fold), Nr4a2 (−1.92-fold), and Tlr4 (−1.85-fold) (Table 9) and numerically but not significantly ($p > 0.05$) the down-regulation of Ptgs2 (Cyclooxygenase-2) (−3.78-fold) support this observation. Angiotensin II is a vasoconstrictor related to hypertension. Angiotensin II is also a potent pro-inflammatory mediator. The inhibition of its converting enzyme, encoded by Ace, has been beneficial in mice pulmonary disease models, and in patients with inflammatory diseases. Asthmatic patients have higher ($p \leq 0.05$) serum levels of angiotensin II converting enzyme compared to controls; it has been proposed that regulating this imbalance may aid in recovering the system's inflammatory and ROS homeostasis. An association has been reported between the severity of CF and the undesirable effects of the Ace gene in Tunisian CF patients. Angiotensin II is associated with the activation of NF-κβ-mediated genes in lung injury. NF-κβ-mediated chronic inflammation is a prominent feature of CF lung disease; its downstream activation of IL-8 secretion and neutrophil influx promote progression of COPD and emphysema.

Our data suggest that AEB GAGs may also exert anti-inflammatory properties through the modulation of Prkce (−2.35-fold) and Nr4a2 (−1.92-fold) (Table 9). Protein kinase C, encoded by Prkce, is involved in signal transduction events for several pathways including immune response, bacterial-induced inflammation, development of COPD, and formation of neutrophil extracellular traps (NET). Excessive NET formation has been associated with inflammation in CF patients. The Prkce downregulation we observed supports the finding of anti-inflammatory effects of AEB GAGs. Nr4a2 is a nuclear receptor regulated by Nfkb1, Tgfb1, Ptgs2, and Tlr4; it modulates inflammation via MMP regulation. In a synoviocyte cell line, microarray analyses showed that Nr4a2 regulates the transcription of the Il8 gene (+5.04-fold increase vs control); it is also a key regulator of inflammation in rheumatoid arthritis in vitro. Streptococcal HA (257 kDa) has anti-inflammatory effects in arthritis, which has been associated with attenuated expression of Nr4a1, Nr4a1, Nr4a3 and Mmp genes. Immune and inflammatory responses can also be mediated by negative regulation of TLRs, which play a role in lung inflammation and in risk of developing emphysema. Our study found the TLRs Tlr2, Tlr4, and Tlr5 were downregulated by AEB GAGS; however only Tlr4 passed the thresholds for statistical significance ($p \leq 0.05$) and fold-regulation (>1.5-fold). NE has been reported to induce 118 gene expression via Tlr4 in human bronchial epithelial cells. In healthy epithelial cells HMW-HA affects TLR2 and TLR4, and protects the integrity of the epithelium by inhibiting apoptosis. In injured tissues, HMW-HA is degraded, shorter fragments promote inflammatory gene expression. These observations support the use of HMW-HA in treating diseased airways, and in modulating inflammation.

The Kit gene encodes a receptor tyrosine kinase which contributes to mast cell adhesion to structural airway epithelial cells. The Kit gene showed the largest down-regulation (−3.88-fold) of all the genes differentially expressed in this study (Table 9). Inhibiting mast cell interactions with structural airway cells can be used as a treatment for asthma. Chronic mast cell activation has undesirable effects on airway function, inflammation, and re-modelling in asthma pathophysiology through the production of TNF-α, IL-1β, IL-6 and IL-13 mediated by TLR4 activation. In both CF and idiopathic pulmonary fibrosis, there are increases in tryptase concentration and in the numbers of chymase positive mast cells in the lungs, symptoms of increased inflammation or fibrosis that correlate with lung function. Mast cell serine proteases (tryptase and chymase) can activate MMP-1. Down-regulation of Ptgs2 (cyclooxygenase-2), which is upregulated in CF, may also reduce the amount of the inflammatory mediator histamine that is released from mast cells. Kit downregulation by AEB GAG treatment can contribute to anti-inflammatory effects and protease/anti-protease balance.

Heat shock proteins (HSP) are produced in response to various forms of cellular stress. HSPs appear to be upregulated during inflammation, for example in asthma epithelial cells. We found that Hsph1 (HSP105), Hsp90aa1 (HSP90a) and Hspa8 (HSP70) were all significantly ($p \leq 0.05$) down-regulated in AEB GAG treated cells by −3.61, −3.35 and −1.94-fold, respectively as compared to control cultures (Table 9). Elevated levels of HSP27, HSP70, and HSP90a in COPD are markers for immune activation and tissue destruction. In patients with COPD, HSP70 and IL-8 levels in lung epithelial tissues are significantly increased. AEB GAG treatment can protect against oxidative stress as suggested by Lcn2 upregulation (2.20-fold) (Table 9). Under conditions of oxidative stress, upregulation of Lcn2 has a protective role against free radicals; its upregulation can be stopped by antioxidants. Lcn2 has been reported to be up to 9.8-fold upregulated in bronchial tissues of individuals exposed to sulfur mustard gas; an advantageous role in decreasing ROS stress has been proposed. Human neutrophil lipocalin-2 is also an antibacterial component of the innate immune system, as well as a biomarker of acute exacerbation in CF. Cxcl1 was also upregulated (3.54-fold) in our study (Table 9); its expression is high in non-asthmatic airway smooth muscle cells in vivo, which limits mast cell chemotaxis. Levels of Cxcl1 are high in BAL of Scnn1b-Tg mice as compared to that from wild-type littermates; however there was no correlation between its upregulation and free levels of DNA or indicators of pulmonary obstruction. Furthermore, this chemokine ligand has been reported to contribute to host defense by modulating neutrophil-related bactericidal functions.

To confirm that our observed upregulated antimicrobial gene expression was not due to contaminants in the AEB GAG preparations (i.e. lipopolysaccharide), the AEB GAG solution was analyzed for *E. coli*/coliforms and total aerobic bacterial counts (data not shown). Aerobic counts (100-10-3 duplicate plates) of the autoclaved treatment solution showed no growth and no coliforms. Aerobic counts of samples prior to autoclaving showed 68 CFU/ml (100× dilution). It is possible that lipopolysaccharides from dead bacteria in the solution could have contributed at least in part to the upregulation of Cxcl1.

Slc9a3r2 (−3.25-fold) and Slc9a3r1 (−2.84-fold) were differentially down-regulated by AEB GAG treatment in Scnn1b-Tg MTEC (Table 9). These genes encode $Na^+$—$H^+$ antiporter regulators in the sub-apical membrane of epithelial cells, where they play a central role in pH regulation and Na+ homeostasis. CFTR and $Na^+$—$H^+$ antiporters in renal epithelial cells interact via a regulatory complex that includes ezrin, encoded by Ezr, and protein kinase A, encoded by Prkaa. Ezr (−3.23-fold), Prkaa1 (−2.42-fold), and Prkaa2 (−2.28-fold) were downregulated by AEB GAG treatment (Table 9). Thus AEB GAGs may help modulate an increased Na+ influx in Scnn1b-Tg by downregulating $Na^+$—$H^+$ antiporter regulators, as well as other components of the regulatory complex. In this manner, the AEB GAGs could help the airway epithelia maintain a more optimal ASL. A Joint Location-Scale Test recently highlighted the role of Slc9a3r1, Slc9a3r2, and Ezr in contributing to CF lung disease. Ezr is highly expressed in the bronchi of humans with chronic airway diseases, and it appears to be essential in NE-induced mucin exocytosis, which can lead to airway obstruction and bacterial colonization. BAL secreted mucin content is increased in Scnn1b-Tg mice. Prkaa1 and Prkaa2 encode adenosine mono-phosphate (AMP)-activated kinase (AMPK). AMPK is an important regulator of cellular energy homeostasis, and it can be activated by hypoxia, oxidative stress, and hyperosmotic stress. The down regulation of Slc9a3r1, Slc9a3r2, Ezr, Prkaa1 and Prkaa2 indicate that AEB GAGS may help mediating Na+ homeostatic balance and improvements in the condition of Scnn1b-Tg MTEC ASL ex-vivo.

Tight junctions between epithelial cells control paracellular movements of water, ions, and solutes, and can regulate cell polarity, and can even play a role in protecting airways from bacterial infection. Hypertonic saline solutions may increase water transport into the ASL, which promotes MCC. A suggested mechanism is the opening of the tight junctions between epithelial cells, which may increase paracellular water transport into the airway lumen. Our observed downregulation of the tight junction protein Tjp1 (~2.69-fold vs control) (Table 9), along with the $Na^+$ balance regulation previously described, may be another indicator of optimization of the ASL conditions through enhanced paracellular permeability. CF airway epithelial cells in vitro have tighter tight junctions than healthy cells. Effects in vivo in the presence of bacterial insults may induce differential expression of Tjp1 and associated proteins. Reports on the effects of HA on tight junctions have been varied.

Other genes that were downregulated with AEB GAG treatment were: Adipor2 (−2.56-fold), Gopc (−2.41-fold), Ppp2r4 (−2.56-fold), Sftpb (−1.94-fold), Calr (−1.79-fold), and Tcf712 (−1.69-fold). Adipor2 (−2.56-fold) (Table 9), which encodes for a receptor of adinopectin, has tissue-dependent and environment-dependent anti- and pro-inflammatory effects. Adinopectin has been proposed as an inflammatory biomarker for COPD, but studies as yet are inconclusive. Gopc, also known as the Golgi-associated PDZ, is a protein involved in vesicle trafficking; it is also a negative regulator of CFTR levels in cellular membranes. Suppression of Gopc has been proposed as an approach to retaining CFTR at the apical membrane. Gopc has been identified as one of the top five genes that predict smoking status. Ppp2r4 is a CFTR-modifier gene that encodes a regulatory subunit of protein phosphatase 2A; it is associated with CFTR deactivation, and it correlates with worsening of $FEV_1$, lung clearance index and effective specific airway resistance in CF patients.

The Sftpb gene has been reported to have conflicting results, both protecting subjects from COPD and increased $FEV_1$, and increasing the risk of acute respiratory failure in COPD. This gene is important in epithelial surfactant homeostasis, and is overexpressed in CF chronic rhinosinusitis and lipopolysaccharide-induced injury. In a 3-year study, surfactant protein B concentrations increased 213% from year 1 to year 3 in CF patients' BAL, a measure that correlated with a decrease in lung function. The concentrations of surfactant proteins A, C, and D remained unchanged during the 3-year period, but there was a progressive loss of their function. In our Scnn1b-Tg ex-vivo study, Sftpb may have been downregulated due to a better monolayer hydration, which might make a reduction in surface tension less critical.

Calreticulin is a protein encoded by the Calr gene. It is involved in Ca' binding as well as protein folding, maturation and trafficking. In COPD and CF airways, endoplasmic reticulum stress and its $Ca^{2+}$ stores (calreticulin) promote $Ca^{2+}$-dependent hyper-inflammatory responses. Some elements of this response are positive, such as protective $Ca^{2+}$-enhanced MCC. However others, such as $Ca^{2+}$-dependent IL-8 secretion, are undesirable. Calr downregulation by AEB GAG treatment of MTEC will help ameliorate these inflammatory effects.

The Tcf712 gene was downregulated −1.69-fold in this study. (Table 9). Expression of this gene correlates with increased risk of diabetes mellitus in the general population, and also with modified age of onset in CF. Tcf712 may play a role in the function of the beta cells of pancreatic islets. An in vivo study in mice suggested that decreased expression of Tcf712 correlates with reduced susceptibility to diabetes, perhaps via regulating the metabolism of glucose and lipids.

The detection limit for TGAse activity in the MTEC culture supernatants in this study was about 0.03 mU TGAse/ml. A linear standard curve ($R^2$=0.992) with triplicate readings in the 0.03 to 0.35 mU/ml range was showed no TGAse activity in any of the samples.

Note that the amount of AEB GAGs used in these experiments (0.5 mg/insert of an extract containing >98.5% HA (~30-1600 kDa)) was much higher than the innate concentrations that have been reported in mice BAL (<5 ng/ml in healthy mice, or 100-120 ng/ml in ozone-exposed mice). The dose applied should thus suffice to compete with any HA present in the MTEC ASL, and to gain access to cell surface receptors. Furthermore, it has been reported that concentrations of CS are low and HS is not detectable in airway secretions, and thus it is unlikely that any innate presence of these GAGs in MTEC ASL contributes to or confounds the results reported here.

CONCLUSIONS

In this research, GAGs were extracted and characterized for the first time from farmed *Alligator mississippiensis*. The extraction and purification methods employed by-product to solvent ratios, protein removal methods, and dialysis times for GAG extraction from alligator waste carcasses, feet and backstraps in combinations that have not previously been used or suggested to extract for GAGs from other sources. A novel process for extracting GAG from alligator eyeball vitreous humor is also reported here.

Of the by-products studied, the alligator carcasses were the bulkiest (942±109 g/farmed alligator), with a total GAG content of 0.60±0.00 mg/g wet carcass. Backstraps had the highest (p≤0.05) GAG yield (15.53±0.27 mg/g wet backstrap). Backstraps were easier to extract due to the simpler structure of the backstrap as compared to the complex structure and composition of carcasses, feet, and eyeballs. The GAGs extracted from all four by-products yield about ~2.13 g total GAGs per harvest-size (~24 cm belly-width) farmed alligator, or an estimated total GAG production of ~0.73 metric tons/year from Louisiana alone (based on the 2014 farm-raised harvest data). Thus alligators are a high yield source of GAGs, comparing favorably to marine sources that are generally perceived as being "clean." The extracts contained 0.72-3.68% protein, with eyeball extracts having the lowest protein content therefore posing a lower risk of likely hypersensitivity reactions in downstream applications. FTIR spectra showed characteristic animal GAG features, including —OH, —NH, —CH peaks; as well as amide peaks from residual protein content. The GAGs in all samples were predominantly (>97%) ns-GAGs or HA with a poly-disperse MW ranging from ~30 to 1600 kDa. High and medium molecular weight GAGs were abundant in the *Alligator mississippiensis* byproducts.

Our Scnn1b-Tg MTEC ex vivo gene expression analysis suggested that alligator eyeball GAGs (0.5 mg/12 mm insert) help recover protease/anti-protease balance through regulation of Slpi (+6.38-fold) and Itga2 (~3.59-fold); help reduce inflammation through regulation of Kit (~3.88-fold), Ace (~3.35-fold), Nfkb1 (~2.96-fold), Nr4a2 (~1.92-fold), and Tlr4 (~1.85-fold); and help regulate ASL osmotic homeostasis through regulation of Slc9a3r2 (−3.25-fold), Slc9a3r1 (−2.84-fold)1, Ezr (−3.23-fold), Prkaa1 (−2.42-fold), and Prkaa2 (−2.28-fold). The regulation of this triad of key factors in dehydrated airways helps lower stress, as indicated by the downregulation of Hsph1 (−3.61-fold), Hsp90aa1 (−3.35-fold), and Hspa8 (−1.94). Our findings are promising for the use of AEB GAGs in ameliorating symptoms of dehydrated airways in CF. Other applications for alligator GAGs include, for example, wound repair, inhibiting tumorigenesis, lung injury repair, skin humectation, and healing of joint disease and arthritis care—in humans, equines, canines, and other mammals.

Example 1. Future Studies

Further in vivo experiments will be conducted to confirm the efficacy of the alligator-derived HA against CF and other inflammatory conditions. Pharmacokinetics will be observed in a mouse model. HA will be injected intravenously into the tail vein of mice. At different time intervals, blood samples will be collected, and the stability of the HA will be assessed using LC-MS. HA will be fluorescently labeled, and biodistribution of the compound in the body will be evaluated. The uptake of HA by lung tissue will be evaluated by fluorescence assay and fluorescence microscopy. HA will be further evaluated in vivo in a transgenic mouse or rat model of CF. Safety pharmacology studies and toxicity studies in animal models will be conducted to estimate the maximum dosage that can be administered without severe side effects.

Mouse or rat models are generally acceptable for determining presumptively safe initial dosages to be tested in Phase I human clinical trials. Dosage transformations from mice to humans are generally based on body surface area. Usually, one-tenth of the $LD_{10}$ is taken as a safe starting point, and dose escalation is performed according to a modified Fibonacci scheme. Toxicity studies will be conducted in FDA-approved facilities. Toxicity studies include acute (single dose), repeated dose (7, 14, 28, 90 days), genetic toxicology (in vitro/in vivo), specialized studies (inhalation, phototoxicity, arthropathy, allergenicity), and safety pharmacology. Reproductive toxicity will also be examined.

Upon completion of these studies, a CF model in non-human primates will be tested, and toxicity will again be assessed.

The animal models provide insight into pharmacological action, pharmacokinetics, dosing, and safety for human patients. Pharmacokinetic studies provide information on the mechanisms of absorption and distribution of the administered drug, the rate at which drug action begins, duration of the effect, chemical changes of the substance in the body (e.g. by enzymes), and the effects and routes of excretion of the metabolites of the drug. In vivo preclinical studies in transgenic animal models are especially helpful since the transgenic animals have diseases similar to those in humans.

The compound(s) will then be tested in human trials in accordance with applicable laws and regulations. The compound(s) will be tested in healthy volunteers at low dosages, followed by Phase II and III clinical trials in CF patients. A powder form for inhalation will be prepared and evaluated, for efficacy in reaching the lung and in ameliorating CF.

DEFINITIONS/GENERAL DISCUSSION

The terminology used herein is for the purpose of describing particular aspects only and is not intended to be limiting. Although any methods and materials similar or equivalent to those described herein can be used in the practice or testing of the present invention; example methods and materials are described herein.

While aspects of the present invention may be described or claimed in a particular statutory class, such as the statutory class of compositions of matter, this is for convenience only and one of skill in the art will understand that each aspect of the present invention can be described and claimed in any statutory class. Unless otherwise expressly stated or clearly implied, it is in no way intended that any method or aspect set forth herein be construed as requiring that its steps be performed in a specific order. Accordingly, where a method claim does not specifically state or clearly imply in the claims or descriptions that the steps are to be limited to a specific order, it is no way intended that an order be inferred. This holds for any possible non-express basis for interpretation, including matters of logic with respect to arrangement of steps or operational flow, plain meaning derived from grammatical organization or punctuation, or the number or type of aspects described in the specification.

As used in the specification and the claims, the singular forms "a," "an" and "the" include plural referents unless the context clearly dictates otherwise; and vice versa.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed, and vice versa. It is also understood that each unit between two particular units is also disclosed. For example, if 10 and 15 are disclosed, then 11, 12, 13, and 14 are also disclosed.

References in the specification and claims to parts by weight (or mass) of a particular element or component in a composition denotes the weight (or mass) relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the compound.

A weight (or mass) percent (wt. %) of a component, unless specifically stated to the contrary, is based on the total weight (or mass) of the formulation or composition in which the component is included.

As used herein, the terms "optional" or "optionally" means that the subsequently described event or circumstance or component may or may not occur or be included, and that the description includes both instances where said event or circumstance or component occurs or is included and instances where it does not.

As used herein, the term "subject" or "patient" can be a vertebrate, such as a mammal, a fish, a bird, a reptile, or an amphibian. Thus, the subject or patient of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses and embryos, whether male or female, are intended to be covered. In one aspect, the subject is a mammal. A "patient" usually refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removing the cause of the associated disease, pathological condition, or disorder. In addition, this term includes palliative treatment, that is, treatment designed for the relief of symptoms with or without curing the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject who is predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician or veterinarian, and been found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injections such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target histamine receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause substantial adverse side effects. The specific therapeutically effective dose level for any particular patient will depend upon a variety of factors including the disorder being treated, the severity of the disorder; the specific composition employed; the age, body weight, general health, sex and diet of the patient; the time of administration; the route of administration; the rate of excretion of the specific compound employed; the duration of the treatment; drugs used in combination or coincidentally with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount," that is, an amount effective for prevention of a disease or condition.

As used herein, "$EC_{50}$" is intended to refer to the concentration of a substance (e.g., a compound or a drug) that is required for 50% antagonism of a biological process, or component of a process, including a protein, subunit, organelle, ribonucleoprotein, etc. In one aspect, an $EC_{50}$ can refer to the concentration of a substance that is required for 50% antagonism in vivo. In a further aspect, $EC_{50}$ refers to the concentration of antagonist that provokes a response halfway between the baseline and maximum response.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

The compounds of the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can coordinate with the compounds of the invention to form hydrates or other solvates. Unless stated to the contrary, the invention includes all such possible hydrates and solvates.

Some compounds have multiple solid phases of matter, sometimes termed polymorphic forms or modifications. The different modifications of a polymorphic substance can differ, sometimes greatly, in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or can be readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated or clearly implied by context, it is not intended that any method set forth herein should be construed as requiring that its steps be performed in a specific order. Accordingly, where a method claim does not actually recite an order to be followed by its steps or it is not otherwise specifically stated in the claims or descriptions that the steps are to be limited to a specific order, it is not intended that an order be inferred, unless clearly required by context. This principle also holds for any possible non-express basis for interpretation, including: matters of logic with respect to arrangement of steps or operational flow; plain meaning derived from grammatical organization or punctuation; and the number or type of embodiments described in the specification. Those of skill in the art will recognize that, in some instances, it is implicit that at least some of the steps of an organic synthesis or of a separation should be carried out in a particular order to produce the desired result.

Disclosed are the components used to prepare the compositions of the invention as well as the compositions themselves to be used within the methods disclosed herein. These and other materials are disclosed herein, and it is understood that when combinations, subsets, interactions, groups, etc. of these materials are disclosed that, while specific reference of each of the various individual and collective combinations and permutations of these compounds cannot be explicitly disclosed, each is specifically contemplated and described herein. For example, if a particular compound is disclosed and discussed and a number of modifications that can be made to a number of molecules including those compounds are discussed, specifically contemplated is each and every combination and permutation of the compound and the modifications that are possible unless specifically indicated to the contrary. Thus, if a class of molecules A, B, and C is disclosed, as well as a class of molecules D, E, and F; and an example of a combination molecule, A-D is disclosed, then even if each is not individually recited each is individually and collectively contemplated, meaning combinations such as A-E, A-F, B-D, B-E, B-F, C-D, C-E, and C-F, etc. Likewise, any subset or combination of such combinations is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

In one aspect, the invention relates to compounds useful for treating CF or other inflammatory conditions. The compound may be supplied in solid form, or dissolved in water or alcohol (preferably ethanol).

The compound may be isolated or prepared in substantially pure form; where, for this purpose, "substantially pure" means that the compound is present in a composition in a concentration (by mass) greater than or equal to: 50%, 55%, 60%, 65%, 70%, 75%, 80%, 85%, 90%, 95%, 96%, 97%, 98%, 99%, 99.5%, 99.7%, or 99.9%.

In one aspect, the disclosed compounds comprise the products of the methods described herein. In a further aspect, the disclosed compounds comprise a compound prepared by a method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

Compounds of the present invention may be administered in pharmaceutical compositions to treat patients (humans and other mammals) with CF or other inflammatory conditions. Thus, the invention includes pharmaceutical compositions containing at least one compound from the present invention and a pharmaceutically acceptable carrier. A composition of the invention may further include at least one other therapeutic agent, for example, a combination formulation or combination of differently formulated active agents for use in a combination therapy method.

The present invention also features methods of using or preparing or formulating such pharmaceutical compositions. The pharmaceutical compositions can be prepared using conventional pharmaceutical excipients and compounding techniques known to those skilled in the art of preparing dosage forms. The compounds of the invention can be administered by oral, parenteral, rectal, topical, or ocular routes, or by inhalation. Preparations may also be designed to provide slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration or oral administration, but more preferably by inhalation.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinylpyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or the compound may be provided as a dry product for reconstitution with water or other suitable vehicles before use. Liquid compositions for oral administration may contain pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents or emulsifiers such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampoules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation containing the compound of the invention and a suitable carrier.

Methods are known in the art for determining effective doses for therapeutic (treatment) and prophylactic (preventative) purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue, system, animal, or human that is being sought by a researcher, veterinarian, medical doctor, or other clinician, which includes alleviation of the symptoms of the disease or disorder being treated. For prophylactic purposes (i.e., preventing or inhibiting the onset or progression of a disorder), the term "effective dose" or "effective amount" or "therapeutically effective dose" or "therapeutically effective amount" refers to that amount of each active compound or pharmaceutical agent, alone or in combination, that inhibits in a subject the onset or progression of CF or other condition as being sought by a researcher, veterinarian, medical doctor, or other clinician. Methods of combination therapy include co-administration of a single formulation containing all active agents; essentially contemporaneous administration of more than one formulation; and administration of two or more active agents separately formulated.

It is expected that a dose of about 15 mg to about 55 mg intravenously three times per week, or about 45 mg to about 150 mg oral three times a week, or about 20 to 50 mg (preferably about 25 mg) inhaled twice daily will be effective for treatment. Expressed as dosage per unit body weight, a typical dose is expected to be between about 0.2 mg/kg and about 0.75 mg/kg (IV), or about 0.6 to about 2 mg/kg (oral), three times per week in either case. Actual dosages may, of course, be adjusted higher or lower depending on clinical observations and outcomes. Alternatively, the doses can be administered at higher frequency earlier in the treatment course, and then adjusted later to a lower frequency—e.g., daily for the first three weeks, and thereafter three times per week.

Compounds of the invention may be orally dosed in the range of about 0.05 to about 50 mg/kg daily, others may be dosed at about 0.05 to about 20 mg/kg daily, while still others may be dosed at 0.1 to about 10 mg/kg daily. Infusion doses can be administered from about 1 to about 1000

µg/kg/min, admixed with a pharmaceutically-acceptable carrier, over a period ranging from several minutes to several days. For topical administration compounds of the present invention may be mixed with a pharmaceutically-acceptable carrier at a concentration of about 0.1% to about 10% of drug to vehicle. For any mode of administration, a preferred molecular weight range is 100 kDa and higher.

Although specific embodiments of this invention have been described herein for purpose of illustration, various modification may be made without departing from the spirit and scope of the invention.

The examples in this specification are put forth to provide those of ordinary skill in the art with a complete disclosure and description of how the compounds, compositions, articles, devices and/or methods claimed herein are made and evaluated. The examples are intended to be exemplary, but not to limit the scope of the invention. Efforts have been made to ensure accuracy with respect to numbers (e.g., amounts, temperature, etc.), but some errors and deviations should be accounted for. Unless indicated otherwise, parts are parts by weight (mass), temperature is measured in the Celsius scale (° C.) or the temperature is ambient temperature, and pressure is at or near one atmosphere.

| ABBREVIATIONS INDEX | |
|---|---|
| ABS | alligator backstraps |
| ACS | alligator carcasses |
| AEB | alligator eyeballs |
| AFT | alligator feet |
| ALI | air-liquid-interface |
| AMP | adenosine mono-phosphate |
| AMPK | AMP-activated kinase |
| ANOVA | analysis of variance |
| ASL | airway surface liquid |
| ATP | adenosine triphosphate |
| BAL | bronchoalveolar lavage |
| BCA | bicinchoninic acid |
| BSA | bovine serum albumin |
| cAMP-PKA | cyclic adenosine monophosphate-dependent protein kinase A |
| CCL27 | cutaneous T cell-attracting chemokine |
| CF | cystic fibrosis |
| CFTR | cystic fibrosis transmembrane conductance regulator |
| ChrAses | chondroitinases |
| COPD | chronic obstructive pulmonary disease |
| CPC | cetylpyridinium chloride |
| CRBD | completely randomized block design |
| CS | chondroitin sulfate |
| CT | threshold cycle |
| DMB | dimethylmethylene blue |
| DMEM | Dulbecco's Modified Eagle Medium |
| DNase | deoxyribonuclease |
| DS | dermatan sulfate |
| ECM | extracellular matrix |
| EDTA | ethylenediaminetetraacetic acid |
| ENaC | epithelial sodium channel |
| FBS | fetal bovine serum |
| FEV1 | forced expiratory volume in 1 second |
| FT-IR | Fourier transform infrared spectroscopy |
| FVC | forced vital capacity |
| GAGs | glycosaminoglycans |
| GalNAc | N-acetylgalactosamine |
| GDC | genomic DNA control |
| GlcA | glucuronic acid |
| GlcNAc | N-acetylglucosamine |
| HA | hyaluronic acid |
| HAases | hyaluronidases |
| HARE | hyaluronan receptor for endocytosis |
| HAS1-3 | hyaluronic acid synthases 1-3 |
| HCl | hydrochloric acid |
| HIV-1 | human immunodeficiency virus type 1 |
| HP | heparin |
| HS | heparan sulfate |
| HSP | heat shock protein |

-continued

| ABBREVIATIONS INDEX | |
|---|---|
| HSV-1 | herpes simplex virus type 1 |
| HMW | high molecular weight |
| HTS | hypertonic saline |
| ICP-AES | inductively coupled plasma atomic emission spectrometry |
| IdA | iduronic acid |
| IL-1β | interleukin 1 beta |
| IL-6 | interleukin 6 |
| IL-8 | interleukin 8 |
| IL-10 | interleukin 10 |
| IRAK | interleukin 1 associated kinase-M |
| KS | keratan sulfate |
| LMW | low molecular weight |
| LYVE1 | lymphatic vessel endothelial hyaluronan receptor 1 |
| MCC | mucociliary clearance |
| MIP-2 | macrophage inflammatory protein 2 |
| MMP | matrix metalloproteinase |
| MMW | medium molecular weight |
| MSD1-2 | membrane spanning domains 1 and 2 |
| MTEC | mouse tracheal epithelial cells |
| MTEC + Y27632 | MTEC media containing Y27632 ROCK inhibitor (10 µM) |
| MTEC + NuSerum | MTEC media containing NuSerum (2%) |
| MWCO | molecular weight cut-off |
| NBD1-2 | nucleotide binding domains |
| NE | neutrophil elastase |
| NF-κβ | nuclear factor kappa beta |
| oHA | hyaluronic acid oligosaccharides |
| PBS | phosphate buffered saline |
| PBST | phosphate buffered saline-Tween |
| PCR | polymerase chain reaction |
| PPARγ | peroxisome proliferator-activated receptor-gamma |
| PPC | positive PCR control |
| R2 | correlation coefficient |
| RD | regulatory domain |
| RHAMM | receptor for hyaluronan mediated motility |
| ROS | reactive oxygen species |
| RTC | reverse-transcription control |
| SD | standard deviation |
| STAT3 | signal transducer and activator of transcription 3 |
| TBE | tris borate-EDTA |
| TCA | trichloroacetic acid |
| TGAse | tissue transglutaminase |
| TLRs | toll-like receptors |
| TNF-α | tumor necrosis factor |
| TSG-6 | tumor necrosis factor-alpha stimulated gene-6 |

The complete disclosures of all references cited in this specification are hereby incorporated by reference. The complete disclosure of the priority applications, 62/612,772 and Ser. No. 16/223,908, are hereby also incorporated by reference in their entirety. Also incorporated by reference is the complete disclosure of Estrada Andino, Jose Daniel, "Extraction and Biochemical Characterization of *Alligator mississippiensis* glycosaminoglycans and an Ex-vivo Murine Pilot Study to Test their Potential Effect on a Selected Panel of Genes Associated with Cystic Fibrosis" (2016). LSU Doctoral Dissertations. 1245, available at digitalcommons.lsu.edu/gradschool_dissertations/1245 (first published online Jan. 8, 2017). In the event of an otherwise irreconcilable conflict, however, the present specification shall control over material that is incorporated by reference.

We claim:

1. A method for extracting hyaluronic acid from *Alligator mississippiensis*, said method comprising the steps of:
   (a) preparing a crude aqueous mixture from one or more hyaluronic-acid-containing components from one or more deceased *Alligator mississippiensis* individuals; wherein the one or more components are selected from the group consisting of all or part of the carcass, backstrap, feet, and eyeballs; wherein the crude aqueous mixture comprises at least some of the hyaluronic acid from the one or more components; and wherein the crude aqueous mixture may contain incidental pathogens;
(b) centrifuging the crude aqueous mixture to separate a liquid supernatant from a solid pellet; wherein the majority of the hyaluronic acid from the crude aqueous mixture partitions with the liquid supernatant; and separating the liquid supernatant containing hyaluronic acid from the solid pellet;
(c) hydrolyzing proteins in the liquid supernatant by enzymatic proteolysis following said centrifuging step, or hydrolyzing proteins in the crude aqueous mixture by enzymatic proteolysis before said centrifuging step, or both;
(d) fractionating the proteolyzed liquid supernatant to separate a selected molecular weight range of hyaluronic acid molecules; and
(e) heating the molecular-weight-range-fractionated hyaluronic acid at a temperature and for a time sufficient to inactivate any pathogens admixed with the separated hyaluronic acid molecules.

2. The method of claim 1, wherein:
(a) the one or more components comprise vitreous humor from one or more *Alligator mississippiensis* eyeballs;
(b) the crude aqueous mixture is prepared by mixing the vitreous humor with water, and homogenizing the vitreous humor/water mixture;
(c) said hydrolyzing step comprises enzymatic proteolysis of the liquid supernatant following said centrifuging step; and
(d) said fractionating step comprises dialyzing the proteolyzed liquid supernatant against water through a semipermeable membrane.

3. The method of claim 1, wherein:
(a) the one or more *Alligator mississippiensis* components are selected from the group consisting of all or part of the carcass, the backstrap, and the feet;
(b) the crude aqueous mixture is prepared by removing any sinews that may be present in the one or more components, or grinding the one or more components, or both; and by bleaching, defatting, and demineralizing; and by mixing with water;
(c) said hydrolyzing step comprises enzymatic proteolysis of the crude aqueous mixture before said centrifuging step;
(d) said fractionating step comprises dialyzing the proteolyzed liquid supernatant against water through a semipermeable membrane;
(e) the method additionally comprises, following said fractionating step, precipitating hyaluronic acid by mixing the dialyzed liquid supernatant with sodium chloride and ethanol;
(f) re-dissolving the precipitated hyaluronic acid in water; and
(g) performing a second centrifuging step on the re-dissolved hyaluronic acid to separate a liquid supernatant from a solid pellet; wherein the majority of the hyaluronic acid partitions with the liquid supernatant.

4. The method of claim 2, additionally comprising the step of freeze-drying the pathogen-inactivated hyaluronic acid solution to produce solid-phase hyaluronic acid.

5. The method of claim 3, additionally comprising the step of freeze-drying the pathogen-inactivated hyaluronic acid solution to produce solid-phase hyaluronic acid.

* * * * *